United States Patent
Yang et al.

(10) Patent No.: US 11,376,080 B2
(45) Date of Patent: Jul. 5, 2022

(54) INTEGRATED ILLUMINATION AND OPTICAL SURFACE TOPOLOGY DETECTION SYSTEM AND METHODS OF USE THEREOF

(71) Applicant: 7D SURGICAL INC., Toronto (CA)

(72) Inventors: Victor X. D. Yang, North York (CA); Adrian Linus Dinesh Mariampillai, Toronto (CA); Beau Anthony Standish, Toronto (CA); Michael Ka Kit Leung, Markham (CA)

(73) Assignee: 7D SURGICAL ULC, Toronto (CA)

( * ) Notice: Subject to any disclaimer, the term of this patent is extended or adjusted under 35 U.S.C. 154(b) by 278 days.

(21) Appl. No.: 16/779,721

(22) Filed: Feb. 3, 2020

(65) Prior Publication Data

US 2020/0246080 A1 Aug. 6, 2020

Related U.S. Application Data

(63) Continuation of application No. 15/270,373, filed on Sep. 20, 2016, now Pat. No. 10,548,672, which is a
(Continued)

(51) Int. Cl.
| | |
|---|---|
| *A61B 34/20* | (2016.01) |
| *A61B 90/35* | (2016.01) |
| *A61B 6/00* | (2006.01) |
| *A61B 5/00* | (2006.01) |
| *G01B 11/25* | (2006.01) |

(Continued)

(52) U.S. Cl.
CPC .......... *A61B 34/20* (2016.02); *A61B 5/0064* (2013.01); *A61B 5/0077* (2013.01); *A61B 6/06* (2013.01); *A61B 6/467* (2013.01); *A61B 6/54* (2013.01); *A61B 50/28* (2016.02); *A61B 90/20* (2016.02); *A61B 90/30* (2016.02); *A61B 90/35* (2016.02); *A61B 90/37* (2016.02); *G01B 11/2513* (2013.01); *G01N 21/4738* (2013.01); *G01N 21/55* (2013.01); *A61B 5/1113* (2013.01); *A61B 5/1128* (2013.01); *A61B 6/544* (2013.01);
(Continued)

(58) Field of Classification Search
CPC ..... A61B 34/20; A61B 5/0064; A61B 5/1113; A61B 5/0077; A61B 90/30; A61B 90/37; A61B 2034/2057
See application file for complete search history.

(56) References Cited

U.S. PATENT DOCUMENTS

| | | | |
|---|---|---|---|
| 7,224,472 B2 | 5/2007 | Bauch et al. | |
| 7,567,833 B2 | 7/2009 | Moctezuma De La Barrera et al. | |

*Primary Examiner* — Jason M Ip
(74) *Attorney, Agent, or Firm* — Hill & Schumacher

(57) ABSTRACT

Systems and methods are provided for optical topology detection and illumination. Embodiments provide an integrated system, and methods of operation thereof, where the integrated system includes an illumination system and an optical topology detection system, and where at least a portion of the spectral content of illumination light from the illumination system is within an optical detection bandwidth of the optical topology detection system, and where the operation of the optical topology detection system and the illumination system are interleaved to avoid crosstalk, such that the optical topology detection system detects the optical topology detection light when the illumination system is not emitting illumination light. The system may include, and control the operation of, an optical navigation system. The components of the system may be mounted to a rigid frame to maintain calibration.

23 Claims, 23 Drawing Sheets

Related U.S. Application Data continuation of application No. 14/439,009, filed as application No. PCT/CA2013/050819 on Oct. 29, 2013, now Pat. No. 9,513,113.

(60) Provisional application No. 61/719,744, filed on Oct. 29, 2012.

(51) Int. Cl.
*A61B 90/30* (2016.01)
*A61B 6/06* (2006.01)
*A61B 90/20* (2016.01)
*G01N 21/47* (2006.01)
*G01N 21/55* (2014.01)
*A61B 50/28* (2016.01)
*A61B 90/00* (2016.01)
*A61B 5/11* (2006.01)

(52) U.S. Cl.
CPC . *A61B 2034/2057* (2016.02); *A61B 2090/309* (2016.02); *A61B 2090/373* (2016.02)

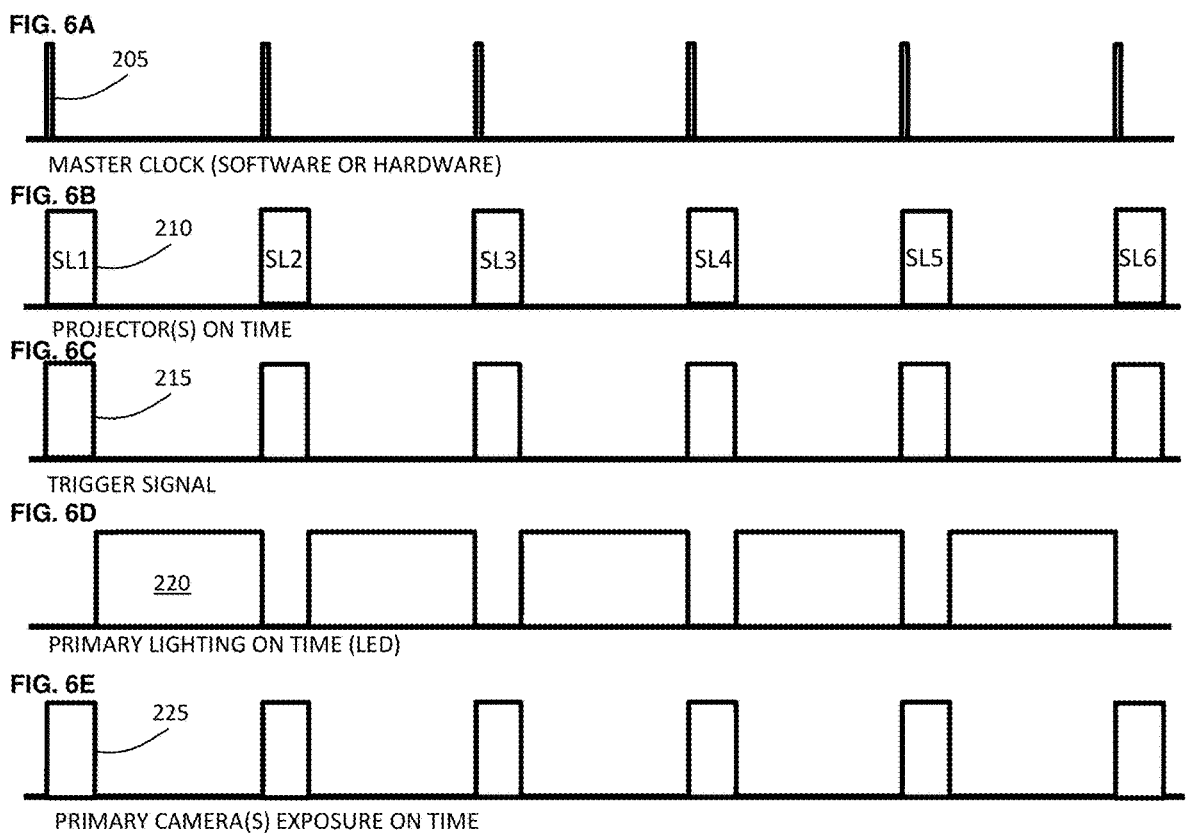

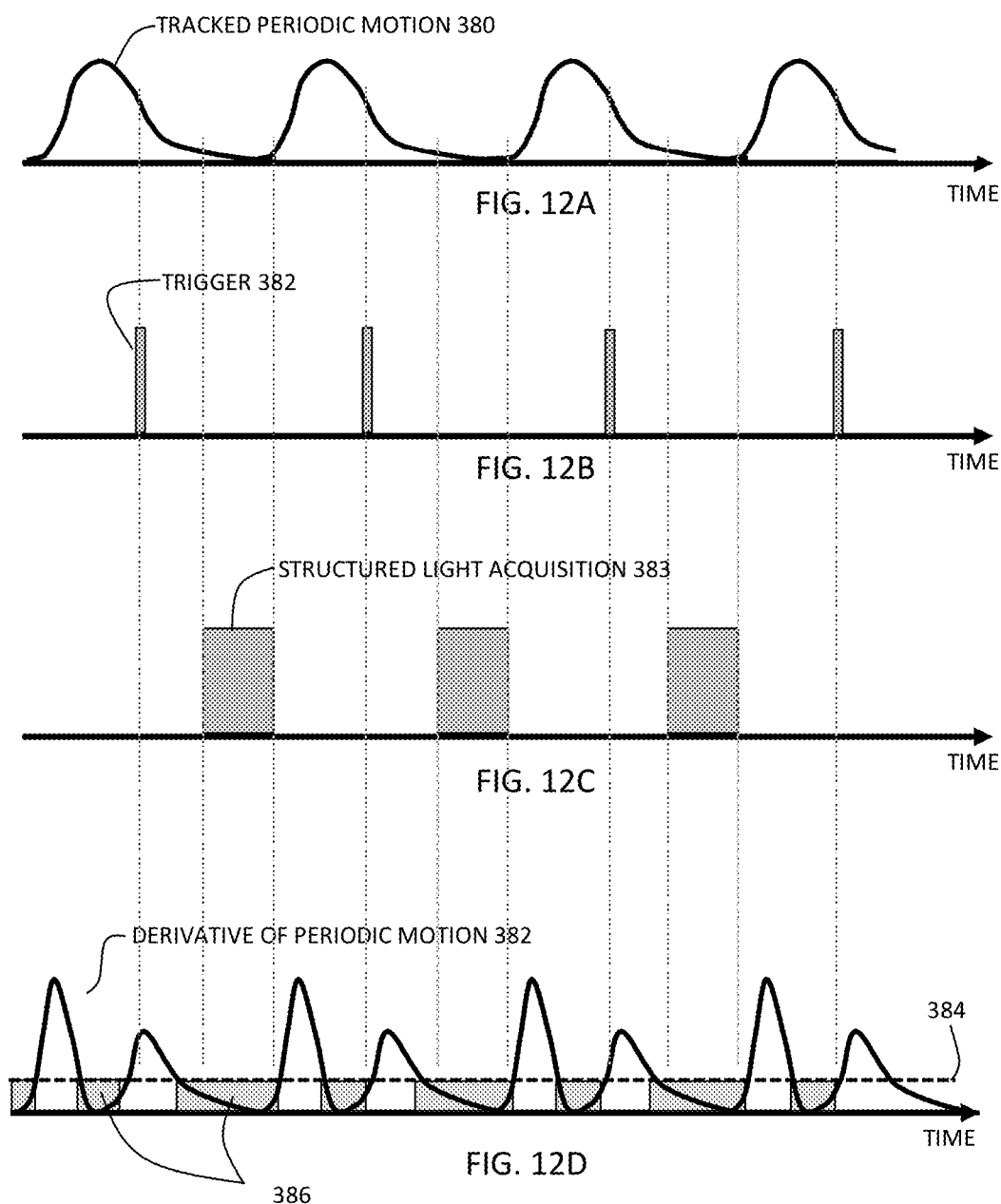

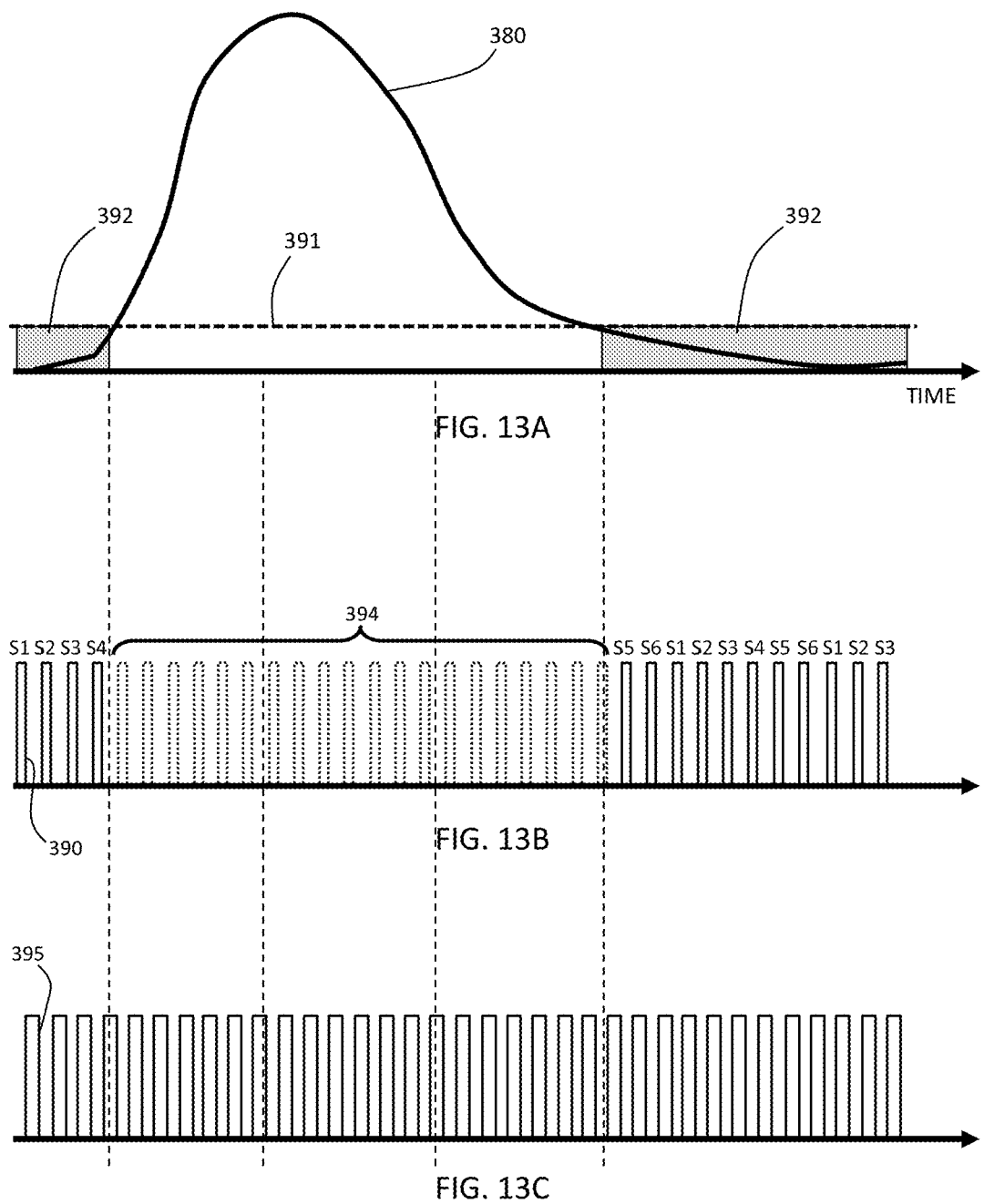

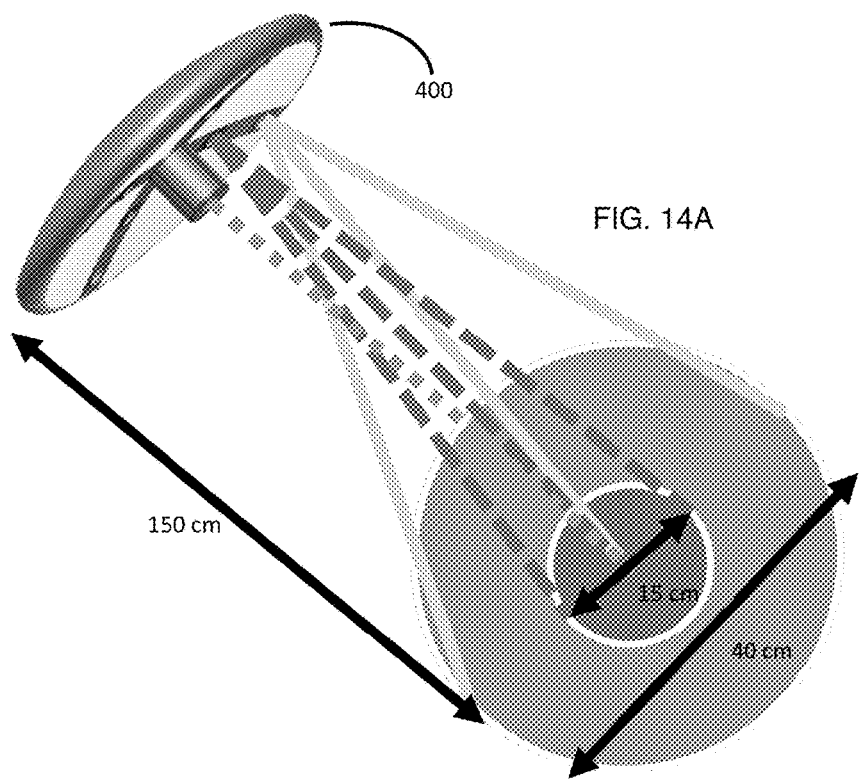
FIG. 14A
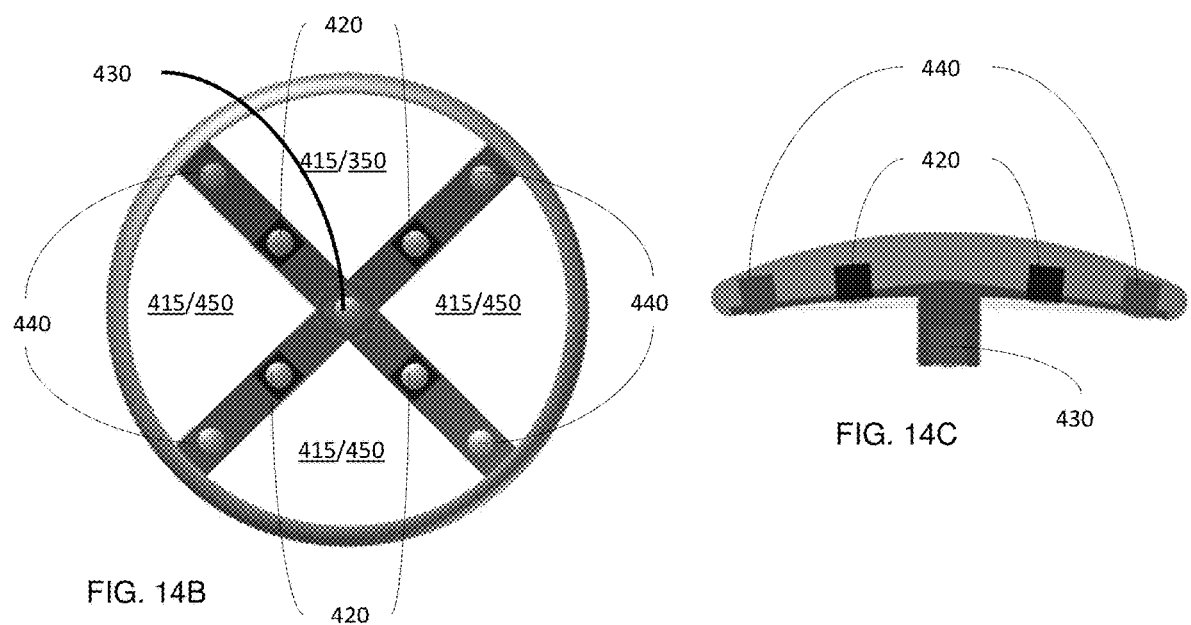
FIG. 14B
FIG. 14C

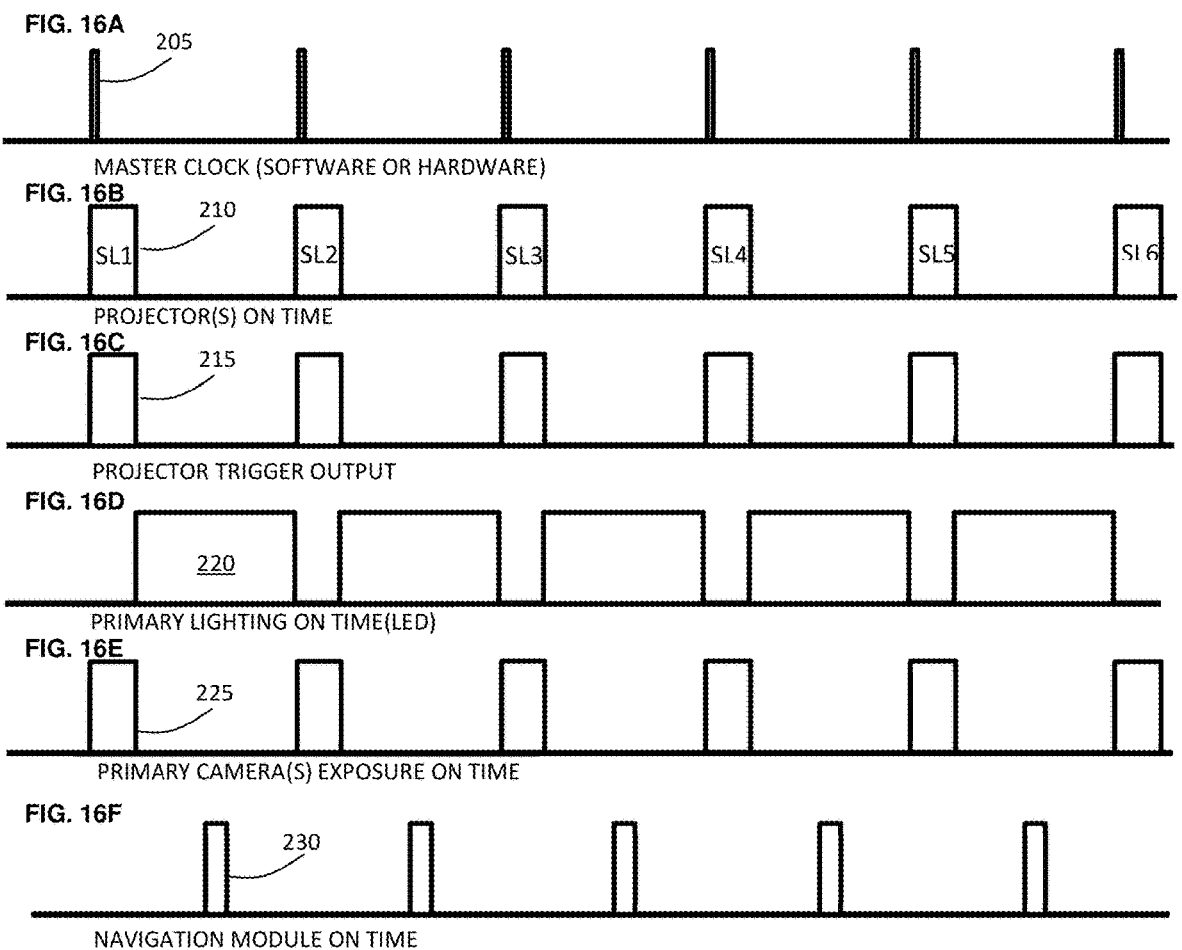

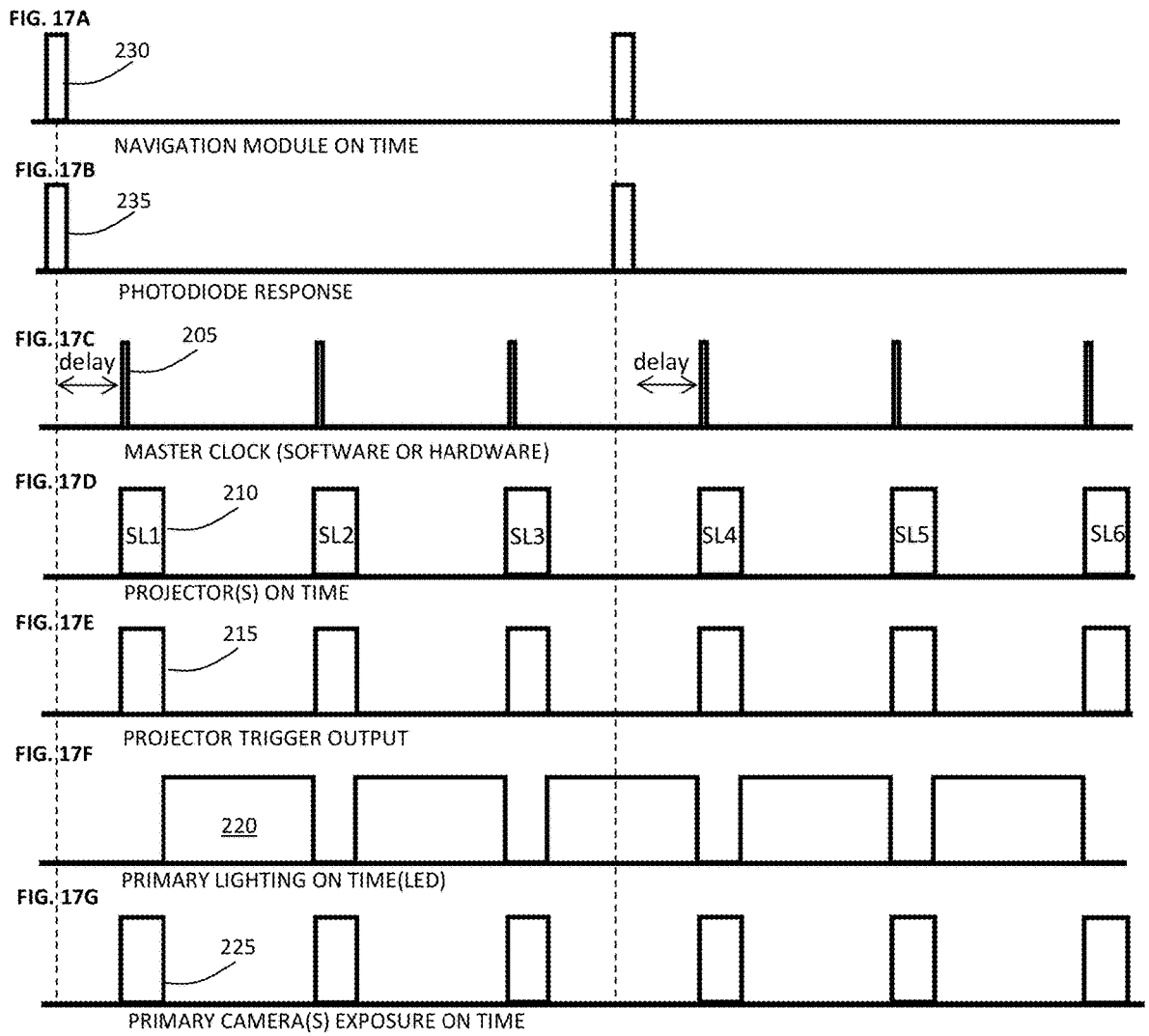

INTEGRATED ILLUMINATION AND OPTICAL SURFACE TOPOLOGY DETECTION SYSTEM AND METHODS OF USE THEREOF

CROSS-REFERENCE TO RELATED APPLICATION

This application claims priority to U.S. Provisional Application No. 61/719,744, titled "INTEGRATED ILLUMINATION AND OPTICAL SURFACE TOPOLOGY DETECTION SYSTEM AND METHODS OF USE THEREOF" and filed on Oct. 29, 2012, the entire contents of which is incorporated herein by reference.

BACKGROUND

The present disclosure relates to optical surface topology detection systems. The present disclosure also relates to surgical illumination and surgical navigation systems.

Optical illumination plays an important role during medical procedures and is especially vital in the surgical theatre, but also important in specialties such as dentistry, ophthalmology and gastroenterology. Lighting sources used in surgical environments typically need to provide bright, uniform, and shadow-free illumination with little visible temporal or spatial modulation. Light emitting diodes (LEDs) are becoming the preferred choice of illumination in medicine due to their high efficiency, long life times and relatively low cost.

Recently, 3D surface topology detection has been successfully applied to a broad range of medical applications including dentistry, orthopedics, surgery, and radiation therapy. This technique provides datasets with sub-millimeter accuracy, which can be used to position the patient for a procedure, design surgical/dental implants, and/or for registration with other imaging modalities to provide subsurface information to the practitioner.

Surface topology datasets can be generated in a number of ways, but typical systems include laser range finders, photogrammetry systems, and structured light imaging systems. For example, stereo structured light imaging can be used to generate surface topology images. This method involves active illumination of the field in order to easily identify correspondences (in images captured by a camera system) when compared to more computationally intensive approaches (such as photogrammetry). Some of the most robust and accurate structured light techniques use sequences of binary patterns, often in conjunction with sinusoidal patterns to further enhance accuracy. To obtain robust reconstructions in the presence of ambient lighting, these methods typically project the inverse binary pattern in order to correctly label pixels.

With recent advances in Digital Light Processing (DLP) technology, the projection of such patterns at very high speeds (1000's of times per second) is now possible. In addition, advances in camera and computing technology have also enabled the synchronized acquisition of these patterns at very high speeds. These recent developments make it practical to perform continuous or snapshot high-speed surface topology imaging of anatomical targets during medical procedures.

Navigation systems are often employed in the surgical theatre, to aid the surgeon performing the procedure by showing the relationship between the patient's current anatomical state and some preoperative or intraoperative images obtained from an imaging modality such as computed tomography (CT). This relationship is visually displayed to the surgeon via a computing and display unit, giving the surgeon subsurface information that they would typically lack without the navigation system.

Most navigation systems are based on optical triangulation of fiducial markers within the tracking unit's field of view. These reflective fiducial markers can be found by illuminating the field of view with a light source, for example, in the near infrared, and viewing the field with a stereo pair of near infrared cameras separated by a baseline, yielding two distinct views of the area (navigation module). Navigation systems may also rely on active fiducial markers, which use near infrared LEDs to emit light that is directly captured by the stereo pair of near infrared cameras. By attaching a plurality of these fiducial markers to a known object, the 3D position and orientation of that object can be determined.

SUMMARY

Systems and methods are provided for optical topology detection and illumination. Embodiments provide an integrated system, and methods of operation thereof, where the integrated system includes an illumination system and an optical topology detection system, and where at least a portion of the spectral content of illumination light from the illumination system is within an optical detection bandwidth of the optical topology detection system, and where the operation of the optical topology detection system and the illumination system are interleaved to avoid crosstalk, such that the optical topology detection system detects the optical topology detection light when the illumination system is not emitting illumination light. The system may include, and control the operation of, an optical navigation system. The components of the system may be mounted to a rigid frame to maintain calibration.

Accordingly, in one aspect, there is provided an integrated surgical system for optical topology detection, illumination, and tracking, comprising:
   a surgical illumination system comprising one or more illumination light sources for illuminating a region of interest with illumination light;
   an optical topology detection system comprising a structured light projection device for projecting optical topology detection light comprising structured light patterns onto the region of interest and one or more optical topology detection cameras for imaging optical topology detection light scattered or reflected from the region of interest; and
   an optical tracking system comprising a plurality of tracking cameras, wherein said optical tracking system is rigidly mounted to said optical topology detection system such that a tracking volume associated with said optical tracking system is fixed relative to an optical topology detection field of said optical topology detection system;
   wherein at least a portion of the spectral content of the illumination light from said surgical illumination system is within an optical detection bandwidth of said optical topology detection system; and
   one or more processors configured to:
      provide one or more control signals for repeatedly triggering interleaved operation of said optical topology detection system with said surgical illumination system; and
      synchronize the operation of said optical topology detection system and said surgical illumination system according to the one or more control signals, such that said optical topology detection system detects optical topology detection light in the absence of the illumination light.

In another aspect, there is provided a method of synchronizing and interleaving the operation of an optical topology detection system, a surgical illumination system, and an optical tracking system for reducing optical crosstalk, wherein the surgical illumination system comprises one or more illumination light sources for illuminating a region of interest with illumination light, the optical topology detection system comprises a structured light projection device for projecting optical topology detection light comprising structured light patterns onto the region of interest, and one or more optical topology detection cameras for imaging optical topology detection light scattered or reflected from the region of interest, and the optical tracking system comprises a plurality of tracking cameras, the method comprising:
- providing one or more control signals for repeatedly triggering interleaved operation of the optical topology detection system with the surgical illumination system and the optical tracking system; and
- synchronizing the operation of the optical topology detection system, the surgical illumination system and the optical tracking system according to the one or more control signals, such that the optical topology detection system detects the optical topology detection light in the absence of illumination light and tracking light;
- wherein at least a portion of the spectral content of the illumination light from the surgical illumination system is within an optical detection bandwidth of the optical topology detection system.

In another aspect, there is provided an integrated surgical system for optical topology detection, illumination, and tracking, comprising:
- a surgical illumination system comprising one or more illumination light sources for illuminating a region of interest with illumination light;
- an optical topology detection system comprising a structured light projection device for projecting optical topology detection light comprising structured light patterns onto the region of interest and one or more optical topology detection cameras for imaging optical topology detection light scattered or reflected from the region of interest; and
- an optical tracking system comprising a plurality of tracking cameras;
- wherein at least a portion of the spectral content of the illumination light from said surgical illumination system is within an optical detection bandwidth of said optical topology detection system; and
- one or more processors configured to:
  - provide one or more control signals for repeatedly triggering interleaved operation of said optical topology detection system with said surgical illumination system and said optical tracking system; and
  - synchronize the operation of said optical topology detection system, said surgical illumination system and said optical tracking system according to the one or more control signals, such that said optical topology detection system detects optical topology detection light in the absence of the illumination light and the tracking light.

In another aspect, there is provided an integrated surgical system for optical topology detection, illumination, and tracking, comprising:
- a surgical illumination system comprising one or more illumination light sources for illuminating a region of interest with illumination light;
- an optical topology detection system comprising a structured light projection device for projecting optical topology detection light comprising structured light patterns onto the region of interest and one or more optical topology detection cameras for imaging optical topology detection light scattered or reflected from the region of interest; and
- an optical tracking system comprising a plurality of tracking cameras;
- wherein at least a portion of the spectral content of the illumination light from said surgical illumination system is within an optical detection bandwidth of said optical topology detection system; and
- one or more processors configured to:
  - provide one or more control signals for repeatedly triggering interleaved operation of said optical topology detection system with said surgical illumination system; and
  - synchronize the operation of said optical topology detection system and said surgical illumination system according to the one or more control signals, such that said optical topology detection system detects optical topology detection light in the absence of the illumination light.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 6A, 6B, 6C, 6D and 6E show a timing diagram showing an example implementation for controlling the illumination and structured light system, including A) master clock, B) projector on time, C) trigger signal, D) primary lighting on time, and E) primary camera(s) exposure on time.

FIG. 12A, FIG. 12B, FIG. 12C and FIG. 12D illustrate an example embodiment in which periodic motion of the patient is monitored for controlling the acquisition of optical topology data, showing A) an example time dependent signal corresponding to the periodic motion, B) a trigger signal, C) the time duration in which structured light is acquired, and D) the derivative of the signal show in A).

FIG. 13A, FIG. 13B and FIG. 13C illustrate an example implementation in which optical topology is only acquired when the periodic motion of the patient is within a prescribed threshold.

FIG. 14A, FIG. 14B and FIG. 14C show a schematic of a variation of system shown in FIGS. 9-11, which the system includes additional cameras for both tool tracking and structured light imaging to increase the robustness of the system to line of sight obstructions.

FIG. 16A, FIG. 16B, FIG. 16C, FIG. 16D, FIG. 16E and FIG. 16F show a timing diagram showing an example implementation for controlling a composite system (lighting, structured light and triangulation system), including A) master clock, B) projector on time, C) trigger signal, D) primary lighting on time, E) primary camera(s) exposure on time, and F) navigation module on time.

FIG. 17A, FIG. 17B, FIG. 17C, FIG. 17D, FIG. 17E, FIG. 17F and FIG. 17G show an additional example embodiment of a timing diagram, when embedded photodiode controls the triggering of the optical topology module and navigation module, which both operate in the NIR spectral regime, showing A) navigation module on time, B) photodiode response, C) master clock, D) projector on time, E) projector trigger output, F) primary lighting on time, and G) primary camera(s) exposure on time.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the term "optical" refers to electromagnetic radiation having a wavelength in the ultraviolet, visible, near-infrared, and/or infrared regions of the electromagnetic spectrum.

Figure 1A:
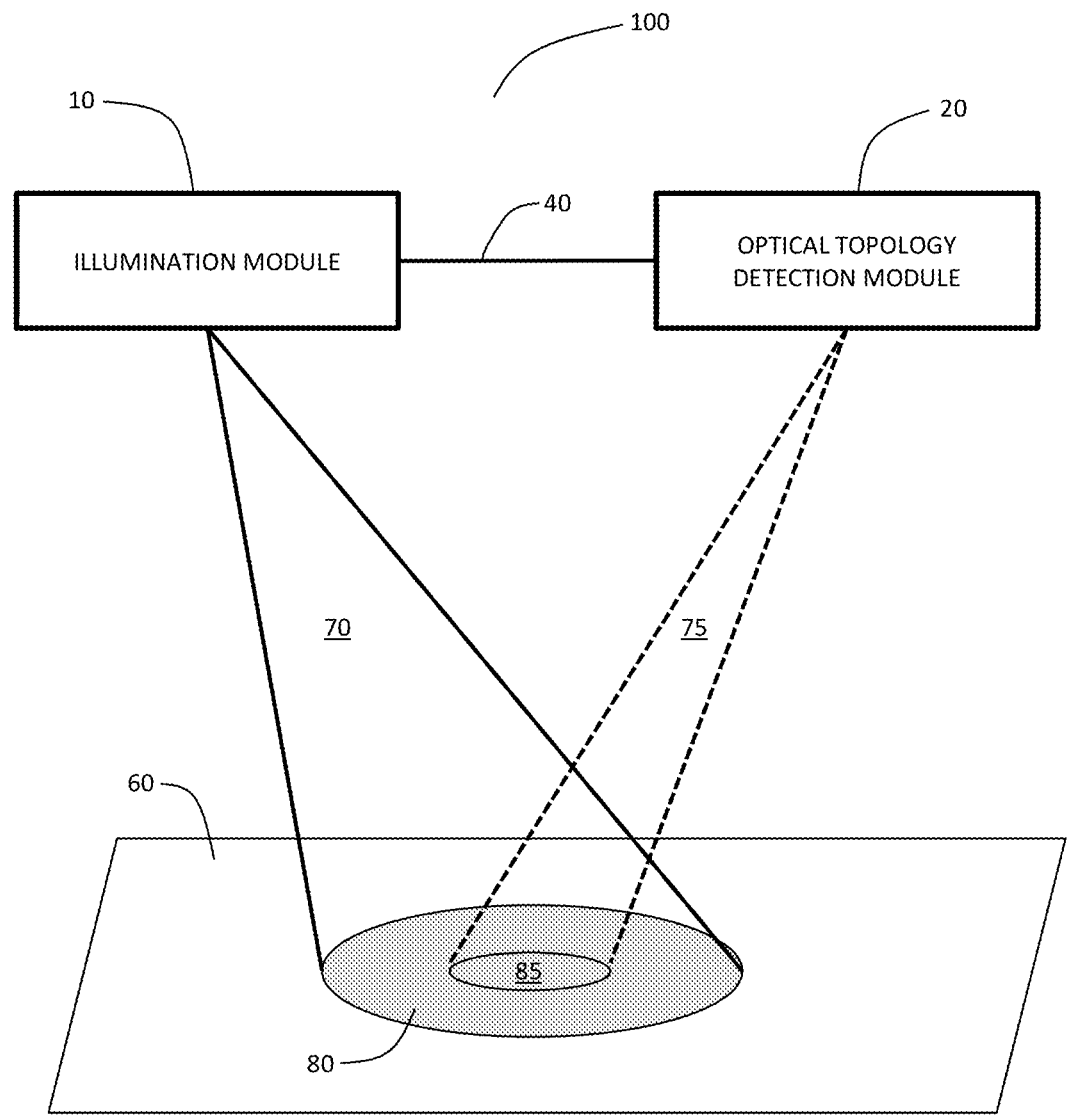
FIGS. 1A and 1B provide schematics diagram of an example composite system, including an illumination module and optical topology detection module, where A) shows a link between the two systems, and B) shows the modules interfaced via a control and processing unit.
Figure 1B:
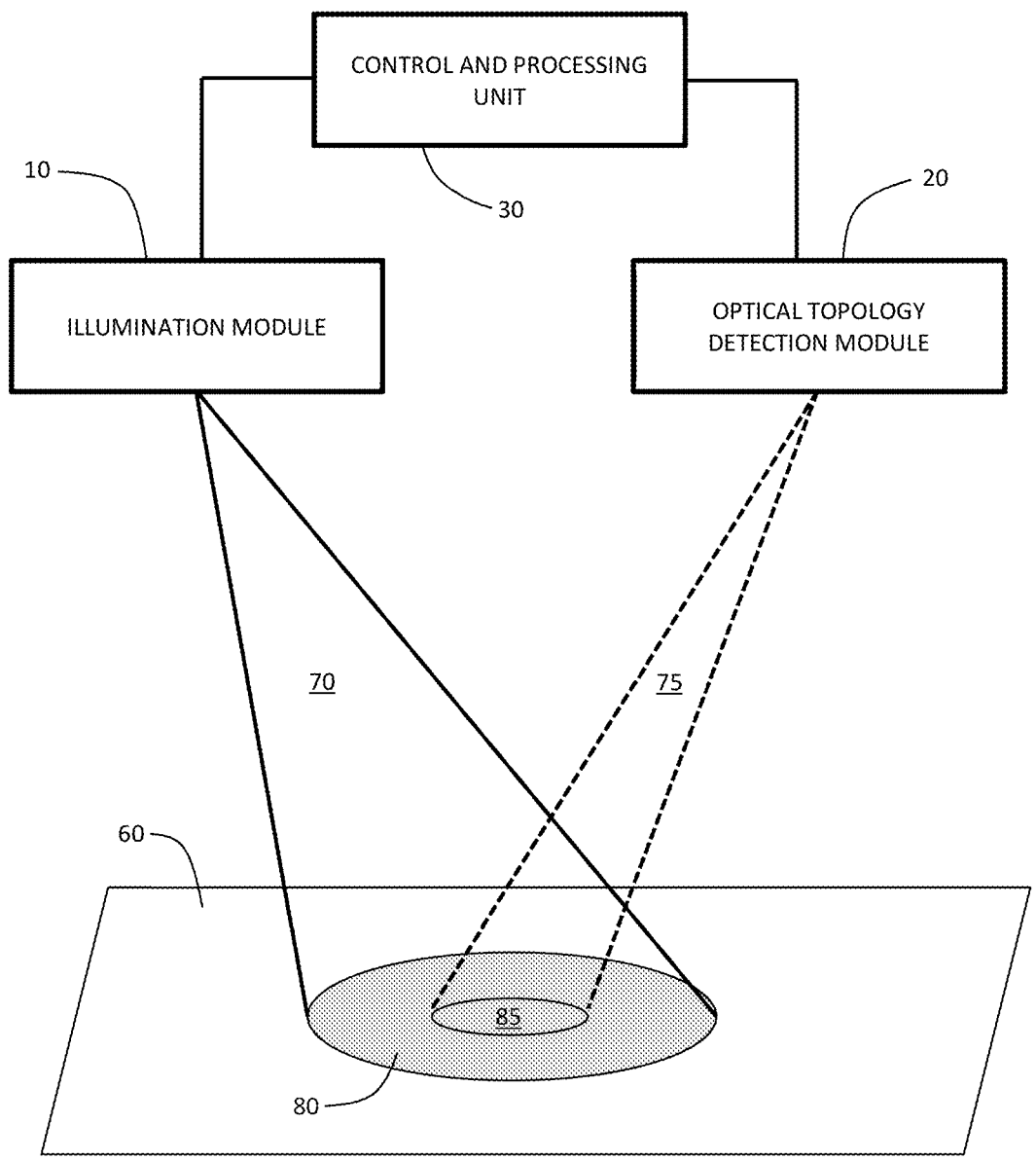

In one embodiment of the present disclosure, an illumination and optical surface topology (also herein referred to as "topology") detection system is provided that avoids mutually-induced optical interference or cross-talk through synchronized illumination and optical surface topology detection. FIG. 1A is a block diagram that illustrates the main components of an example system 100, including illumination module 10 and optical topology detection module 20, which are interfaced or connected as shown through connection 40. As shown in FIG. 1B, illumination module 10 and optical topology detection module 20 may be interfaced through external control and processing unit 30, which may reside externally from optical topology detection module 20.

Illumination module 10 and optical topology detection module 20 are supported such that optical topology detection field 85 of optical topology detection module 20 is positioned to illumination field 80 of illumination module 10. This may be achieved, in one example implementation, by rigidly supporting illumination module 10 and optical topology detection module 20, for example, on a common rigid frame, mechanical support, or housing. In particular, as shown in FIG. 1A, illumination module 10 may be positioned such that the center of optical topology detection field 85 is approximately aligned with the center of specified illumination field 80. In surgical applications, the center of optical topology detection field 85 may be positioned relative to the center of illumination area 80, such that the center of the specified area to be illuminated (anatomy, implant, tool etc.) is also the target for optical topology imaging.

In another example implementation, illumination module 10 need not be fixed related to the optical topology detection module 20. For example, illumination module 10 may be, or may include, a portable illumination device, such as a light placed on a helmet wearable by a surgeon. In such an embodiment, the illumination module need only be configured such that illumination field 80 is positionable to overlap with optical topology detection field 85. In such an embodiment, the interface between illumination module 10 and optical detection module 20 (and optional control and processing unit 30) may be a wireless link (as described below).

In another example embodiment the optical topology detection system 20 need not be fixed mechanically to the illumination module 10 but rather the relative position of the optical topology detection field 85 is aligned dynamically with respect to the illumination field 80 through a motorized system consisting of components such as motors, servo's, actuators, hydraulics for motion and a sensing system based on position tracking sensors (RF, Optical, EM, or mechanical etc.).

According to various embodiments, both illumination module 10 and optical topology module 20 are operated on a time-dependent basis, such that when illumination module 10 is emitting illumination light, optical topology module 20 is not emitting topology detection light, and vice versa. As described below, connection 40 and/or control and processing unit 30 is employed to synchronize the operation of illumination module 10 and optical topology module 20. By synchronizing the operation of illumination module 10 and optical topology module 20, optical topology image data is acquired in the absence of interfering light from illumination module 10. Furthermore, in some embodiments, the intensity and/or duration of topology detection light emitted by optical topology detection module 20 is controlled relative to the intensity and/or duration of illumination light emitted by illumination module, such that the ratio of the time averaged (i.e. as perceived by a human observer) illuminance of the topology detection light to the perceived time averaged illuminance of the illumination light is sufficiently small that the fluctuations in optical power associated with the topology detection system are substantially imperceptible to a human observer.

Figure 2:
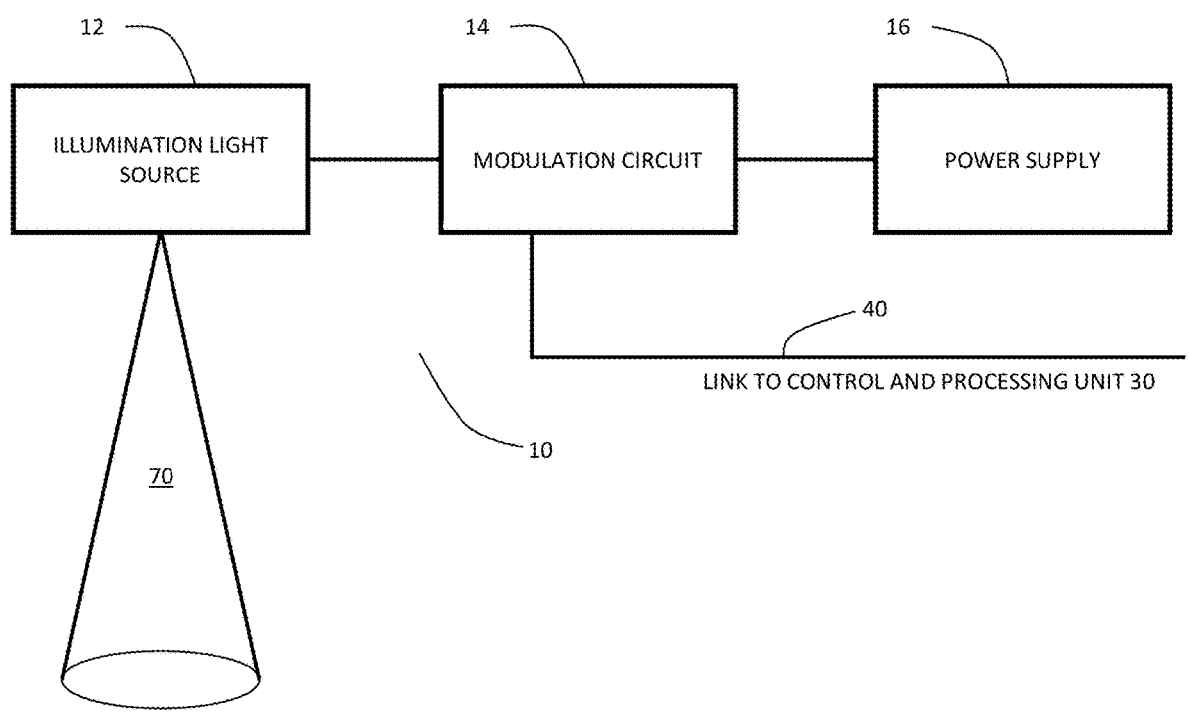
FIG. 2 is an optical block diagram showing an example implementation of the illumination module.

An example embodiment of illumination module 10 is shown in FIG. 2. In the present example embodiment, illumination module 10 includes illumination light source 12, modulation circuit 14, and internal power supply 16. In another embodiment, power may alternatively be provided to illumination module 10 from an external power source without the need for an internal power supply.

In one embodiment, illumination light source 12 may include one or more LEDs. An example of a suitable LED light source is one or more Cree XP-G Neutral White LEDs. The LEDs may be provided in an array, such as a circumferential or ring array. Illumination light source 12 may also include suitable focusing and/or beam conditioning optics (not shown) for producing an optical beam with a suitable beam shape and/or divergence angle.

Example illumination module 10 also includes modulation circuit 14 for temporally modulating the optical power emitted by illumination light source 12. This may be achieved, for example, by modulating electrical power provided to illumination light source 12, which in turn causes the optical power emitted by illumination light source 12 to be optically modulated. Alternatively, modulation circuit 14 may be employed to directly modulate the optical power emitted by illumination light source 12 (for example, by controlling an optical shutter, beam chopper, or other optical modulation device).

In one embodiment in which illumination light source 12 includes LEDs, modulation circuit 14 may include an LED controller circuit, such as Linear Technology LT3476EUHF high power current driver with pulse width modulation, for modulating the electrical current delivered to the LEDs. In other embodiments, modulated electrical current may be externally supplied to illumination module 10 from an external control circuit, such as from control and processing unit 30 shown in FIG. 1B.

Figure 3:
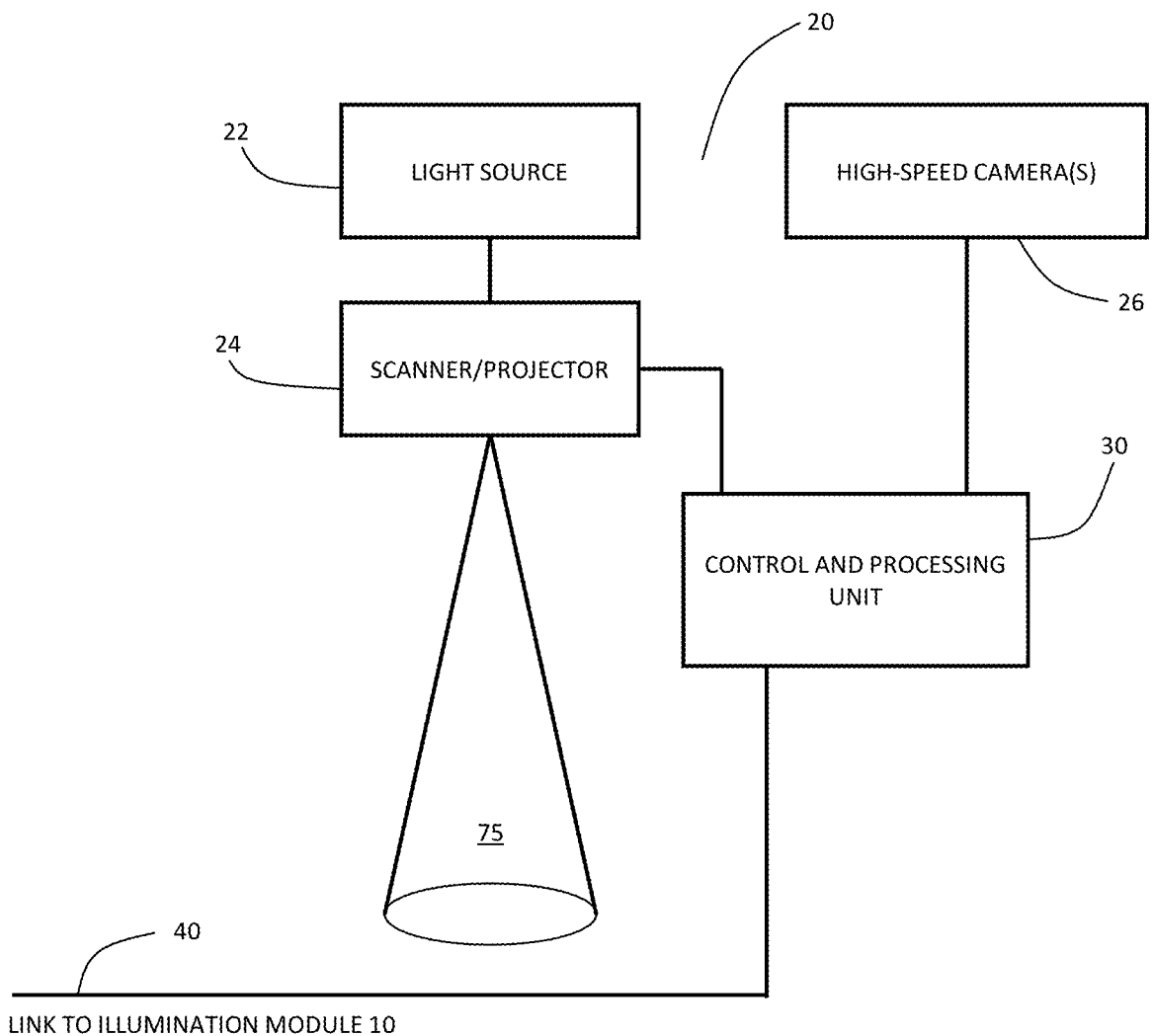
FIG. 3 is a block diagram showing an example implementation of the optical topology detection module.

As shown in FIGS. 2 and 3, modulation circuit 14 is connected to control and processing unit 30 (which may be integrated within optical topology detection module 20, as shown in FIG. 1A, or provided as or in a separate device, as shown in FIG. 1B. Connection 40 may be a physical cable (e.g. for delivering an electrical or optical signal), or may be a wireless connection, for example, as an optical transmission modality, or wireless transmission modality such as Wifi, Bluetooth, NFC or Zigbee®. Connection 40 allows transmission of signals and/or data between the system modules in order to facilitate temporal synchronization of the modules, as described further below.

In one example implementation, connection 40 may be a unidirectional connection between control and processing unit 30 and modulation circuit 14, for example, the delivery of a modulation signal that is synchronized with the acquisition of optical topology detection. In another example embodiment, the connection may be unidirectional between modulation circuit 14 and control and processing unit 30, for example, for synchronizing the acquisition of optical topology detection data with time-dependent illumination. In another example implementation, the connection may be a bidirectional connection.

Optical topology detection module 20 may be any suitable system for detecting, measuring, imaging, or otherwise determining surface topology of one or more objects using optical radiation. Non-limiting examples of suitable optical devices include laser range finders, photogrammetry systems, and structured light imaging systems, which project optical topology detection light onto a region of interest, and detect optical topology detection light that is scattered or reflected from the region of interest, as described in PCT Application No. PCT/CA2011/050257, titled "SYSTEM AND METHODS FOR INTRAOPERATIVE GUIDANCE FEEDBACK", which is herein incorporated by reference in its entirety.

FIG. 3 illustrates an example embodiment in which optical topology system 20 is a structured light imaging system that includes light source 22, scanner or projector 24, one or more high-speed cameras 26, and control and processing unit 30. Structured light projector 24 may be any device suitable for projecting (for example, by imaging or scanning) light from light source 22 in a structured light pattern onto a surface of interest. An example of a suitable structured light projector is a Digital Light Processing (DLP) device. Light source 22 and scanner/projector 24 may be integrated in a single device, such as the DLP LightCrafter. Such a device can be modified to project white light by replacing the blue LED with a white light LED and removing the dichroic mirror (for example, a Cree XM-L Neutral white LED). Alternatively, red, green and blue LED's may be run simultaneously or sequentially and in varying proportions to produce visibly white light (or other colors) with varying color temperatures to approximately match the illumination module output. Alternatively RGB laser's may be substituted for LED's.

In one embodiment, camera 26 is a triggerable camera. It is to be understood that while one camera 26 is shown in the figure, alternative embodiments may include two or more cameras. Camera 26 may be a color or monochrome camera and may be based on CMOS or CCD technologies. The imaging speed of the camera is important for situations where motion may occur that disrupts structured light acquisition. For example, in surgical applications a typical respiratory rate of a patient during surgery is P breaths per minute. For a structured light sequence using n patterns, the acquisition should occur in less than a fraction S of the respiratory period necessitating a camera with a minimum triggerable acquisition speed of approximately $(n \times P)/(60 \times S)$ fps. Thus, for a respiratory rate of P=20, a structured light sequence using n=24, and S=1/30 results in a minimum triggerable acquisition speed of 240 fps.

It is noted that during triggerable acquisition, the frame rate of the camera may be decreased from the camera's untriggered mode. For other applications, such high imaging speeds may not be needed and this number may be reduced to a framerate which simply makes visible disruptions negligible.

In one example embodiment, camera 26 is a high-speed camera that is electronically linked to a structured light projector 24 in order to synchronize acquisition of the images with the projection. One example of a suitable camera is the Point Grey Flea3 camera which is a monochrome CMOS camera, capable of triggerable acquisition of greater than 300 Hz at 640×480 pixel resolution. The camera is connected to the control and processing unit 30 via a USB 3.0 interface for high speed data transfer.

Figure 4:
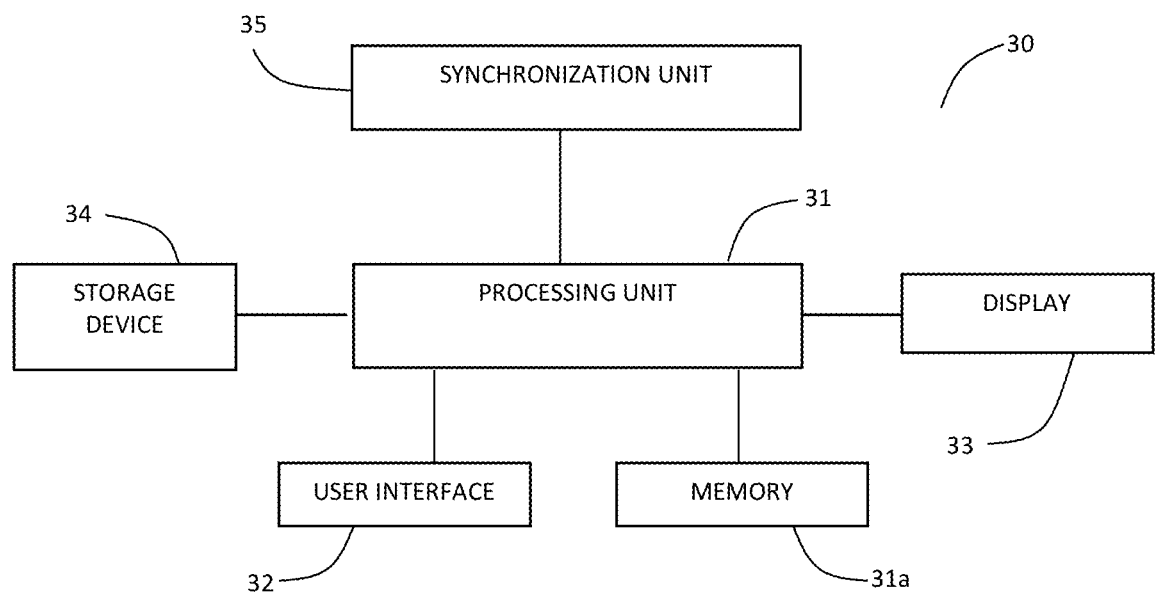
FIG. 4 is a block diagram showing an example implementation of the control and processing unit.

FIG. 4 shows an example embodiment of control and processing unit 30, which may include computer hardware such as a processing unit 31 (e.g. one or more processors) and associated memory 31a containing one or more computer programs to control the operation of the system, where processing unit 31 is in communication with a user interface unit 32 and display 33. In one example, the control and processing unit 30 may be a computing system such as a personal computer or other computing device, for example in the form of a computer workstation, incorporating a hardware processor and memory, where computations are performed by the processor in accordance with computer programs stored in the memory to carry out the methods such as initiation of structured light imaging and reconstruction of acquired images into surface topology. For example, the processor can be a central processing unit or a graphical processing unit, or a combination of a central processing unit or graphical processing unit. Data from these methods may be stored on a device storage unit 34.

The instructions to control illumination module 10 and/or the optical topology module 20 may be generated by processing unit 31. Alternatively, control and processing unit 30 may contain a synchronization unit 35, which may be used to output various instructions to the illumination module 10 and/or the optical topology module 20. For example, the synchronization unit 35 could take the form of one or more additional processors, which may be linked to processing unit 31 via serial communication or another connection method (wi-fi, usb, Ethernet, Bluetooth etc.). Alternatively, the synchronization unit 35 may be an analogue or digital data acquisition (DAQ) card. The instructions can be transmitted to the illumination module 10 and/or optical topology module 20 in the form of various digital and/or analog communication methods and protocols, such as, for example, electrical, optical, acoustical or other methods.

In one embodiment, control and processing unit 30 includes a general purpose computer or any other hardware equivalents. Thus, the system may include at least one processor (CPU/microprocessor), a memory, which may include random access memory (RAM), one or more storage devices (e.g., a tape drive, a floppy drive, a hard disk drive or a compact disk drive), and/or read only memory (ROM), and various input/output devices (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a position tracked probe, a foot switch, 6-degree input device based on the position tracking of a handheld device, and the like, and/or a microphone for capturing speech commands, etc.). The control and processing unit 30 may also be implemented as one or more physical devices that are coupled to the CPU through a communication channel. For example, the control and processing unit 30 can be implemented using application specific integrated circuits (ASIC). Alternatively, control and processing unit 30 can be implemented as a combination of hardware and software, where the software is loaded into the processor from the memory or over a network connection. In one embodiment, control and processing 30 (including associated data structures) of the present disclosure can be stored on a computer readable medium, e.g., RAM memory, magnetic or optical drive or diskette and the like.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROMS), Digital Versatile Disks, (DVDs), etc.), among others. The instructions can be embodied in digital and analog communication links for electrical, optical, acoustical or other forms of propagated signals, such as carrier waves, infrared signals, digital signals, etc. A machine readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.). As used herein, the phrases "computer readable material" and "computer readable storage medium" refers to all computer-readable media, except for a transitory propagating signal per se.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's).

As shown in FIG. 1B, control and processing unit 30 may reside external to illumination module 10 and optical topology detection module 20. The projection of structured light patterns by structured light projector 24 and detection and processing of structured light images by camera 26 is coordinated by control and processing unit 30.

Figure 5A:
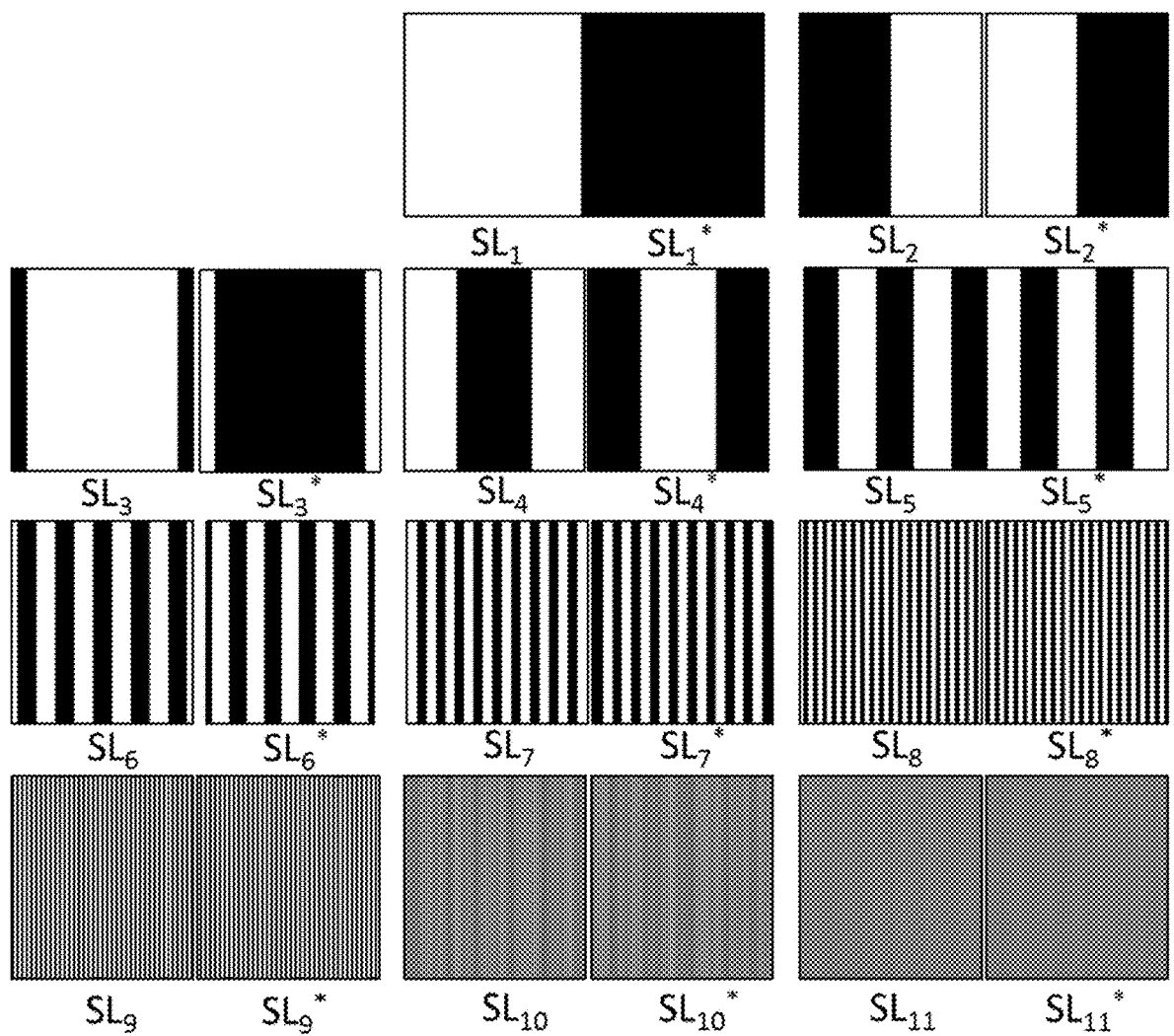
FIGS. 5A, 5B and 5C are illustrations showing schematics of structured light sequence utilizing A) Gray codes, B) phase shifted sinusoids and C) combination of Gray codes and phase shifted sinusoids.

In one example implementation, as shown in FIG. 5A, structured light scanning is performed using a Gray code pattern ($SL_i$) and their inverses ($SL^*_i$). While it is not essential to project the pattern and its inverse to reconstruct the surfaces, projection of the inverse allows a more robust reconstruction in highly scattering environments and in the presence of ambient lighting. The sequence of images in FIG. 5A shows a full column encoded set of fringes for a 608 column DLP projection system, with the largest fringe being 608 pixels wide and smallest having a width of 2 pixels. An important benefit of Gray code scanning and reconstruction methods is the method's robustness to step height variations.

Figure 5B:
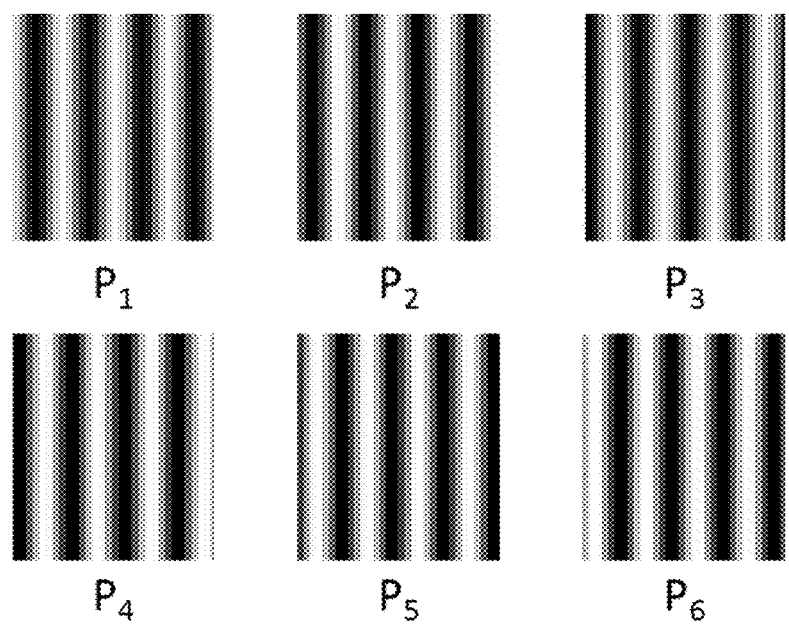

In another example implementation, structured light scanning can also be performed by projection of a set of phase shifted sinusoidal patterns. FIG. 5B shows a zoomed in view of such a set of phase patterns with a period of 8 pixels and shifts of 60 degrees between images. The advantage of phase shifting methods is the reconstruction of denser point clouds relative to Gray code methods (reconstruction yield point clouds at the full camera resolution). However, phase shifting methods require the use of computationally expensive phase unwrapping routines which may not be suitable for all applications.

Figure 5C:
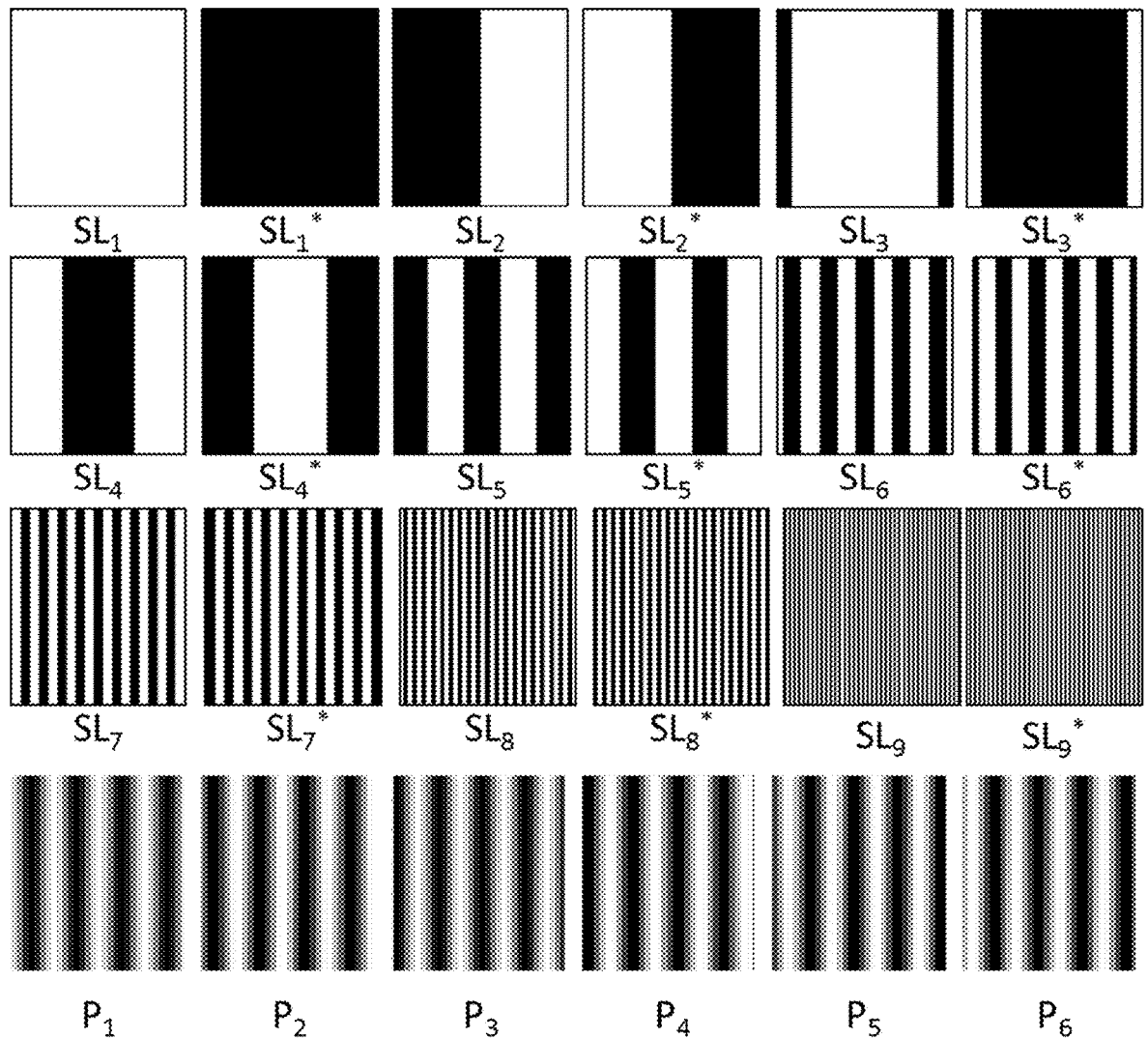

In other example embodiments, Gray codes and phase shifting methods may also be combined to obtain robust reconstruction in presence of step height discontinuities while enabling dense reconstructions. FIG. 5C shows an example of the set of images needed for such a system. Coarse reconstruction is performed by projection of the first 8 levels of the Gray code sequence followed by 6 phase images to further refine the reconstruction and to obtain a dense reconstruction while avoiding the computationally intensive phase unwrapping technique (at the expense of having to project the additional Gray code patterns).

Other example pattern codification schemes for structured light scanning include the use of binary patterns (opposed to Gray codes), n-ary codes, De Brujin sequences, M-arrays, gray levels and color encoding. In some embodiments, illumination module 10 emits light that has a spectral component that would lie within the spectral bandwidth of light detection of optical topology detection module 20 (i.e. at least a portion of the spectral content of the illumination module overlaps with an optical detection bandwidth of the optical topology detection module). In order to avoid a compromised signal to noise ratio during optical detection of the surface topology, the emission of light by illumination module 10 is synchronized with the operation of optical topology detection module 20, such that optical topology detection module 20 only detects surface topology when illumination module 10 is not emitting light. An example implementation of this synchronization in the non-limiting case of structured light topology detection is shown in FIGS. 6A to 6E which provides timing diagrams that illustrate the synchronized and temporally interleaved operation of the two modules.

FIG. 6A shows a master clock signal 205 that is employed to repeatedly trigger structured light projector 24 to project a pattern during time interval 210, as shown in FIG. 6B, optionally in an ordered sequence of patterns (as described above). Master clock signal 205 can, for example, be generated from hardware (for example, via a function generator such as Agilent 3320A or embedded microcontroller) or software/firmware (for example, via computing module 30). As shown in FIGS. 6C and 6E, trigger signal 215 is provided from computing module 30 to camera 26, which repeatedly signals camera 26 to acquire structured light images during time interval 225.

The on-time of the illumination module is shown in FIG. 6D. In this particular embodiment, the illumination module is triggered by the falling edge of trigger signal 215. For example, the trigger signal 215 can be used to generate a modulation/PWM signal which is sent to the illumination module (such as a LED driver). To achieve optimal SNR during optical topology detection, the illumination lighting is turned off completely during the camera/projector on time 225. However, for practical reasons binary modulation (on/off) of the illumination modulation may not be achievable.

For example, in medical applications, stringent electromagnetic compatibility requirements are enforced to prevent accidental interference of one piece of medical equipment with another. A reduction in EM emissions could be achieved by reducing the slew rate associated with modulation of LEDs employed for illumination. The reduction in slew rate can be achieved, for example, by (1) prolonging the amount of time it takes to turn on and turn off of the LEDs, and/or (2) reducing or increasing the maximum and/or minimum output intensity, respectively, of the illumination module. Implementation of either or both of these methods could lead to incomplete turn off of the LED illumination module during optical topology acquisition.

It is to be understood that a wide variety of triggering and synchronizations implementations may be employed according to embodiments of the present disclosure. For example, one or more triggering signals may be generated by control and processing unit 30 for synchronizing the interleaved operation of the optical topology detection module 20 and illumination module 10.

In another example, illumination module 10 may repeatedly illuminate the region of interest during time interval 220, and a control signal may be generated by a processor associated with illumination module 10 and provided to trigger the operation of optical topology detection module 20 when illumination module 10 is not emitting the illumination light.

In another embodiment, optical topology detection module 20 may repeatedly project optical topology detection light onto the region of interest, and a control signals may be generated by a processor associated with optical topology detection module 20 and provided to trigger the operation of illumination module 10 such that illumination module 10 does not emit the illumination light during the operation of optical topology detection module 20.

In one embodiment, one or more control or trigger signals may be generated directly by an optical source or projector associated with optical topology module 20, such as structured light projector 24, and employed to control camera 24 and/or illumination module 10. In another example implementation, a control or trigger signal 215 may be provided to structured light projector 24, instead of master clock signal 205, in order to control the duration of the projection of structured light patterns.

In another example implementation, the camera 26 may be triggered by master clock signal 205 to activate the optical topology system and perform the camera exposure during a prescribed time interval 225. Camera 26 may in turn output trigger signal 215 which in turn may be used trigger structured light projector 24 during time interval 210, and/or to control the timing of illumination module 10. As noted above, it is to be understood by those skilled in the art that other triggering methods and synchronization protocols may be employed in alternative embodiments.

Trigger signal 215 (which need not be periodic) may also be provided to modulation circuit 14 in order to turn off, or lower, the intensity of, illumination light emitted by illumination module 10. As described above, this synchronization of the systems is achieved through connection 40 between modulation circuit 14 of illumination module 10 and control unit 30 (which may reside within, or external to, optical topology detection module 20).

In the example implementation shown in FIGS. 6A to 6E (and in related variations described above), a single pattern is projected during the illumination off-time (i.e. during each time interval 210 between illumination cycles 220, with a different pattern $SL_i$ per time interval). In principle, however, any number of patterns (e.g. two or more patterns, or all of the patterns) may be projected and acquired during a given interval 210 between illumination cycles, given fast enough projector and camera systems. Thus it is to be understood that in other embodiments, a full sequence of structured light patterns may be divided into sub-sequences of patterns, such that two or more patterns are projected (and acquired) during each time interval 210.

Accordingly, by synchronizing, and temporally interleaving the operation of the two systems, optical topology detection may be performed by optical topology detection system 20 without cross-talk or interference from illumination module 10. The time interval between successive cycles (i.e. the time duration between master clock pulses) may be sufficiently short as to render this invisible to an observer. For example, the time interval may be less than approximately 10 ms.

In some embodiments, the modulation frequency of the illumination module is chosen to render flickering effects invisible to an observer, such that the illumination light is perceived as being continuous in time by an observer. It is generally known that above approximately 60-100 Hz (depending on the observer and the modulation depth), human vision is unable to perceive flickering effects, relatively independent of the duty cycle and modulation depth (the range of light output between the high/on and low/off levels in a flickering light waveform). Accordingly, the frequency of modulation of the illumination light is selected to be sufficiently high that the fluctuations in the light intensity would be rendered invisible to an observer. For example, in some embodiments, the frequency of modulation of the illumination light is greater than approximately 60 Hz. In other embodiments, the frequency of modulation of the illumination light is greater than approximately 100 Hz. In other embodiments, the frequency of modulation of the illumination light is selected to be greater than 200 Hz, 500 Hz, or higher frequencies.

However, due to a stroboscopic phenomenon known as saccadic masking, a visual phenomenon caused by aliasing that occurs when continuous motion is represented by a series of short or instantaneous samples, high spatial frequency components of the projected patterns may still transiently visible to the human eye, even at projection rates exceeding 1000 Hz. Accordingly, when using active projection (for example, structured light projection), patterns projected using visible light can produce visual disruptions to an observer, due to such saccadic masking effects. In some embodiments, such stroboscopic effects may be reduced by reducing the modulation depth between high and low cycles. In other instances, these stroboscopic effects may be of secondary importance to flickering as these effects only become apparent when viewing quickly moving objects within the illumination field.

In some embodiments, LEDs are employed for illumination in order to achieved very fast response times (typically <1 μs), thereby enabling temporal modulation of intensity at very high speeds (Hz-MHz), which may help reduce flickering and stroboscopic effects. In some embodiments, the illumination intensity is modulated at a frequency exceeding 1 kHz, while in other embodiments, the illumination intensity is modulated at a frequency exceeding 1 MHz.

In some embodiments, in which illumination module 10 and optical topology detection module 20 emit visible light (i.e. in which optical topology detection module is an active system), the duration and/or intensity and/or sequence of the emitted topology detection light patterns are controlled relative to the duration and/or intensity of the illumination light, in order to reduce visual disruptions, such that the ratio of the time averaged (i.e. as perceived by a human observer) illuminance of the topology detection light to the perceived time averaged illuminance of the illumination light is sufficiently small that the fluctuations in optical power associated with the topology detection system are substantially imperceptible to a human observer. This is achieved through the synchronization and control of the two modules.

The time averaged illuminance, can be expressed according to the following example equation:

$$\overline{E_v} = \int_0^T E_v(t)dt$$

where T is chosen to be much larger than the time taken to cycle through all the patterns in the sequence.

For example, structured light imaging can be performed by the projection of the sequence of Gray coded images shown in FIG. 5A. When projecting this particular sequence of patterns at frame rates ranging between 100 and 240 fps, it was determined experimentally, that the time averaged illuminance ratio (averaged over a timescale much longer than the inverse of the maximum frequency perceivable by a human observer, for example, longer than 100 milliseconds) between the illumination module 10 and optical topology detection module 20 should be on the order of approximately 100:1, or greater, in order to adequately mask the projected patterns and reduce visual disruptions.

In another realization of the system 100, structured light imaging is performed with a sequence of phase patterns shown schematically in FIG. 5B. By projection of these sinusoidal fringes at frame rates between and 100 and 240 fps it was found experimentally that the time averaged illuminance ratio (averaged over a timescale much longer than the inverse of the maximum frequency perceivable by a human observer) between the illumination system 10 and the optical topology system 20 required to mask the projected patterns was on the order of approximately 50:1 or greater.

Figure 7:
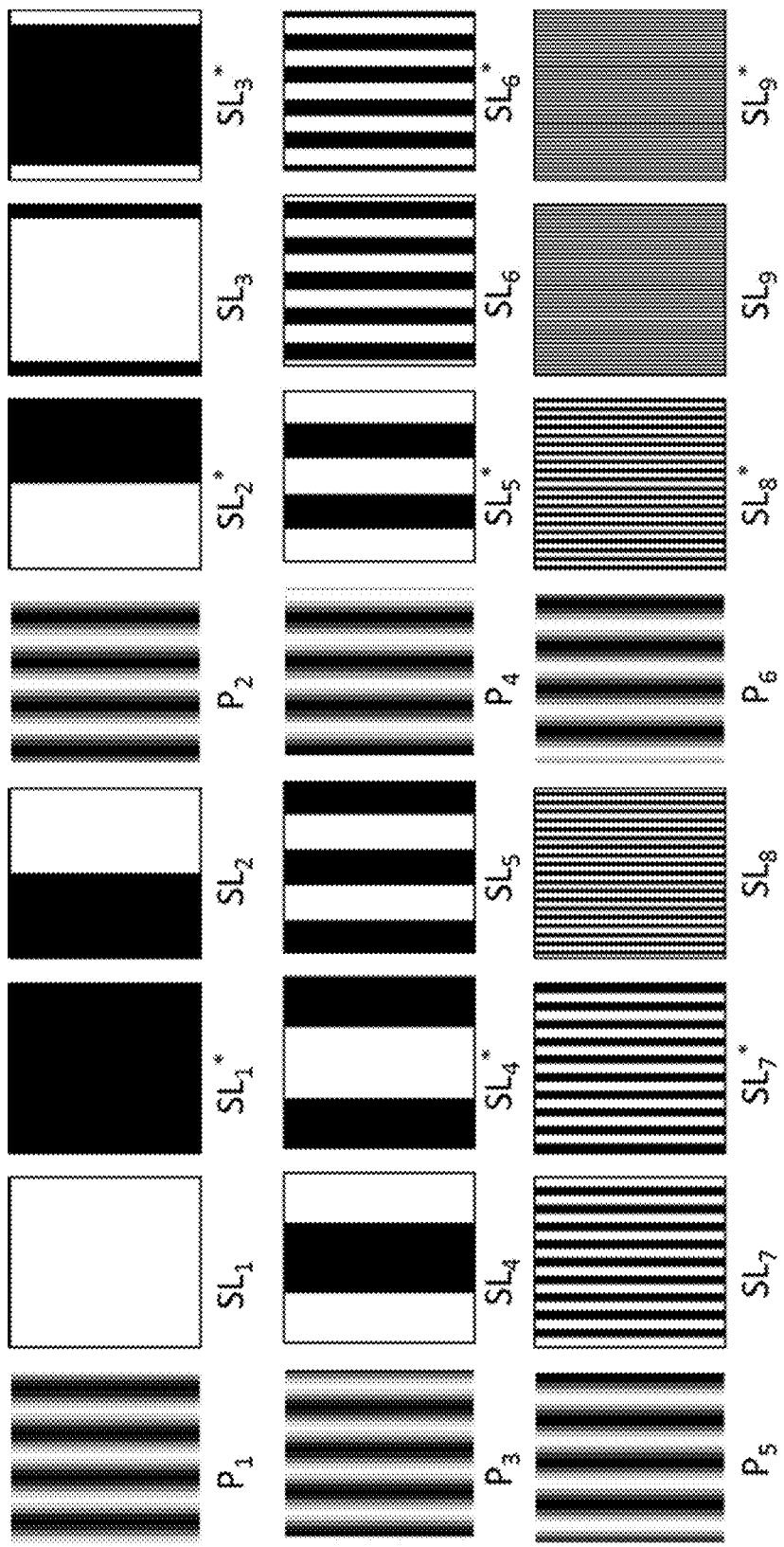
FIG. 7 is an illustration showing a schematic of an ordering of structured light utilizing combined Gray code and phase shifted sinusoids.

In yet another realization of the system, structured light imaging is performed using a sequence of Gray code and phase images shown schematically in FIG. 5C. In this case it was experimentally found that the required time averaged illuminance ratio (averaged over a timescale much longer than the inverse of the maximum frequency perceivable by a human observer) between the two modules was on the order of approximately 200:1 or greater. However, by changing the order of the projected patterns from the sequence shown in FIG. 5C to the sequence shown in FIG. 7, this ratio can be reduced to 100:1. This is beneficial as it is crucial to maximize the photons acquired by camera 26 during spatial light projection.

These example implementations illustrate that the particular orderings of the pattern sequence can provide a further increase in the projected intensity of topology detection light for a given lighting illumination intensity, thus maximizing the camera acquisition SNR. This may be particularly important in a situation where limits may be placed on the lighting illumination, such as in the case of surgical lighting where illumination must typically be between 40000 and 160000 lux.

It is noted that while the above threshold values for the time averaged illuminance ratio (averaged over a timescale much longer than the inverse of the maximum frequency perceivable by a human observer) between the two modules have been specified for frame rates between 100 and 240 fps. Rapid technological advances have led to increases in LED intensity, DLP projection rates, camera acquisition rates and camera sensitivities will enable faster acquisition, while still maintaining high SNR using shorter exposures. These increases in imaging speed will ultimately lead to a further reduction of threshold values necessary to achieve masking of the SL pattern sequences.

In the case of continuous projection rates approaching approximately 10000 Hz, visual disturbances (both stroboscopic and flicker) due to SL pattern sequences would no longer be perceptible, even if the illumination module intensity were to go to zero. That is, regardless of the presence or absence of the illumination module, any visual disturbance due to SL pattern sequences would be negligible. The preceding statement assumes that the length ($N_s$) of the pattern sequence is less than approximately 100 frames. This implies changes in the time averaged intensity during a single pattern sequence would have a frequency greater than 100 Hz (10000 Hz/$N_s$) and thus would not be visible.

Furthermore, if one assumes a linear scaling for the threshold value of the time averaged illuminance ratio (averaged over a timescale much longer than the inverse of the maximum frequency perceivable by a human observer) for a particular pattern sequences, one can determine an example generalized scaling expression (based on the example frequency of 10,000 Hz noted above) for the particular pattern sequence needed to achieve masking, namely:

$$T_S(f_{proj}) = T_S(f_m) - \frac{T_S(f_m)}{10000 - f_m} \times (f_{proj} - f_m)$$

where $T_S$ is the threshold value for the particular pattern sequence, $f_{proj}$ is the projection framerate and $T_S(f_m)$ is the measured threshold value for the particular pattern sequence at a projection frequency of $f_m$ Hz. In some embodiments, illumination module 10 is operated during illumination time interval 220, and turned completely off during time interval 215 such that a substantial portion of the time interval between subsequent cycles is available for active optical topology detection. By selecting the relative time durations 210 and 220, and the relative optical intensities of the two modules, optical topology patterns may be projected with sufficiently low intensity during interval 210 such that the visual disturbances are substantially reduced or no longer detectable by an observer, but projected over a sufficiently long time during the interval that cameras 26 may integrate the optical signal to capture images of the low intensity projected patterns with a sufficiently high signal to noise ratio for topology reconstruction. In some embodiments, the collection of light by camera 26 during this portion of the interval may be enhanced by having the camera aperture completely open to increase the amount of light captured during the short integration time, and/or employing light gathering optical components such as lenses, mirrors and filters.

The image acquisition speed, which puts a limit on the integration time of the camera, as well as the intensity of the projected light, and the camera aperture, are adjustable parameters in the acquisition of structured light images. In one example, after fixing the image acquisition speed (for example, for a given camera selection), the maximum allowable integration time may be employed, as this offers better signal to noise ratio when compared to a shorter integration time. For similar reasons, in some embodiments, the intensity of the projected light could be set to the maximum supported by the projector to achieve a high signal-to-noise ratio, which typically occurs at values much less than that from the surgical lights. The camera's aperture is also a variable parameter and in the case where camera integration time and projector intensity is maximized the aperture can be chosen in such a way to maximize depth of field and signal-to-noise ratio, while not saturating the camera. Once these parameters are chosen they are typically fixed, as changing the aperture alters the calibration of the system.

This leaves the gain of the system as the most easily adjustable parameter in a calibrated system in a practical clinical setting. The gain may be automatically set by acquiring an image from the working surgical field, and selecting a setting such that the fraction of camera pixels that are saturated are below a predefined threshold. For example, the gain setting may be modified so that less than 20% of the pixels are saturated.

It is to be understood that optical topology detection module 20, whether active (emitting and detecting light) or passive (only detecting light), need not employ emission or detection of light in the visible spectrum. For example, in some embodiments, optical topology detection module 20 emits and detects light in the infrared spectrum (for example, in the near-infrared (NIR) spectrum). Even though illumination module 10 is generally employed for the illumination of a region with visible light, many visible light sources also emit significant amounts of optical radiation outside of the visible spectrum (such as in the infrared and/or ultraviolet spectral ranges). Accordingly, the preceding embodiments may be employed when a visible optical illumination module 10 is synchronized with a non-visible (e.g. infrared or ultraviolet) optical topology detection module 20, in order to reduce or avoid out-of-band crosstalk or interference.

Furthermore, it is to be understood that illumination module 10 is not limited to providing illumination in the visible spectrum. For example, the system may be employed for machine vision applications that require infrared illumination. In such cases, an embodiment in which illumination module 10 provided infrared illumination would be useful.

It is further noted that although in some cases, optical filtering may be employed to eliminate or suppress out-of-band crosstalk, there may be situations or applications in which this is not possible or convenient. For example, in a surgical environment, multiple illumination sources may be employed, and two or more of the multiple illumination sources may be controlled according to the preceding embodiments. It may not be practical or convenient to provide optical filtering to suppress out-of-band emission for each illumination source.

In other embodiments, other light emitting and/or detection systems or devices may be synchronized and temporally modulated and controlled to avoid or suppress crosstalk or interference among systems. Non-limiting examples are therapeutic modalities like surgical lasers, photodynamic therapy, laser ablation, low level laser therapy, infrared thermal therapy systems. Non-limiting examples of diagnostic optical modalities devices include fluorescence and/or luminescence imaging systems, scattering-based imaging systems such as optical coherence tomography, diffuse optical spectroscopy, Raman, coherent anti-Stokes Raman spectroscopy, dynamic light scattering, laser scattering spectroscopy, diffuse optical tomography, photo-acoustic imaging.

It is to be understood that one or more other light emitting and/or detection systems or devices may be controlled in place of the optical topology detection system, or, in addition to the optical detection system. For example, in one embodiment in which an additional light emitting device is controlled in addition to the optical topology detection module, the operation of the additional light emitting device may be temporally multiplexed with the operation of optical illumination module 10 and optical topology detection system 20, in a serial manner similar to that shown in FIG. 4, and as illustrated in the example provided below. Alternatively, if the operation of the additional light emitting device is compatible with either optical illumination module 10 or with optical topology detection module 10, the additional light emitting device may be operated simultaneously with the module with which its operation is compatible.

Figure 8A:
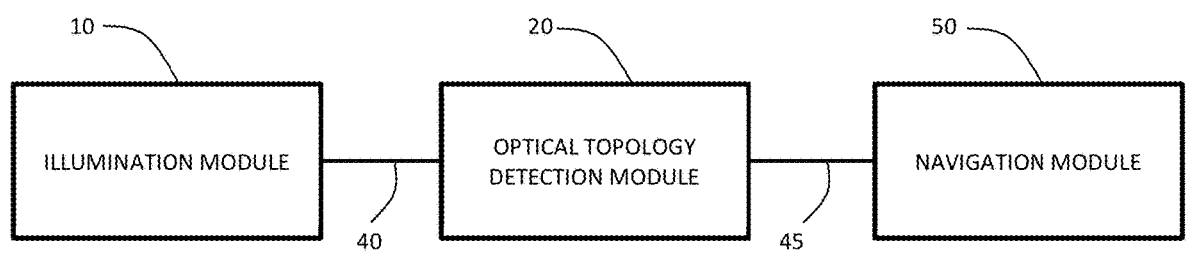
FIG. 8A is a block diagram showing an example implementation of a composite system showing shadow free illumination module, optical topology detection module and navigation module as well as links between systems.

An example of an additional optical system that may be interfaced with both optical illumination module 10 and with optical topology detection system 20 is schematically shown in FIG. 8A in which the additional optical system is a surgical navigation (tracking) module 50. Surgical navigation module 50 performs referencing of the spatial position and orientation of objects. As shown below, all three modules may be linked in such a way to enable synchronization of all three modules, to allow for temporally controlled and gated illumination, imaging and referencing to be performed.

In one embodiment, navigation module 50 may also be rigidly attached to topology detection module 20 in such a way such that the tracking volume is fixed to a selected position relative to the optical topology detection field in such a way such that the tracking volume is fixed relative to the optical topology detection field, which enables simultaneous positioning and calibrated operation of navigation module 50 and optical topology detection module 20. Navigation module 50 and/or the optical topology detection module 20 may also be rigidly attached illumination module in such a way such that the tracking volume is fixed to a selected position relative to either the illumination field and the optical topology detection field, which enables simultaneous positioning and calibrated operation of all three optical modules.

Optical surgical navigation systems typically employ passive or active optical triangulation. For example, surgical navigation systems commonly employ two stereotactic cameras to detect the positions of passive optical fiducial markers (e.g. reflective spheres) and/or active optical fiducial markers (e.g. light emitting diodes (LEDs)). Such systems often employ infrared-based passive and active triangulation, and large quantities of near infrared background, whether from large amount of stray light and/or by having a large imaging volume, can reduce the accuracy of triangulation.

In the example embodiment shown in FIG. 8A illumination module 10 is a surgical lighting system, for example, providing substantially shadow-free illumination, and as described above. Optical topology detection module 20, also described above, may be a structured light imaging system based on a stereo calibrated camera pair and projection unit, which may employ a combination of binary patterns and their inverses. As shown in the FIG. 8A, optical topology detection module 20 is connected to illumination module 10 via connection 40 for synchronized operation.

In addition to these two modules, navigation module 50 is also synchronized via connection 45 with optical topology detection module 20 in order to minimize crosstalk and interference.

Figure 8B:
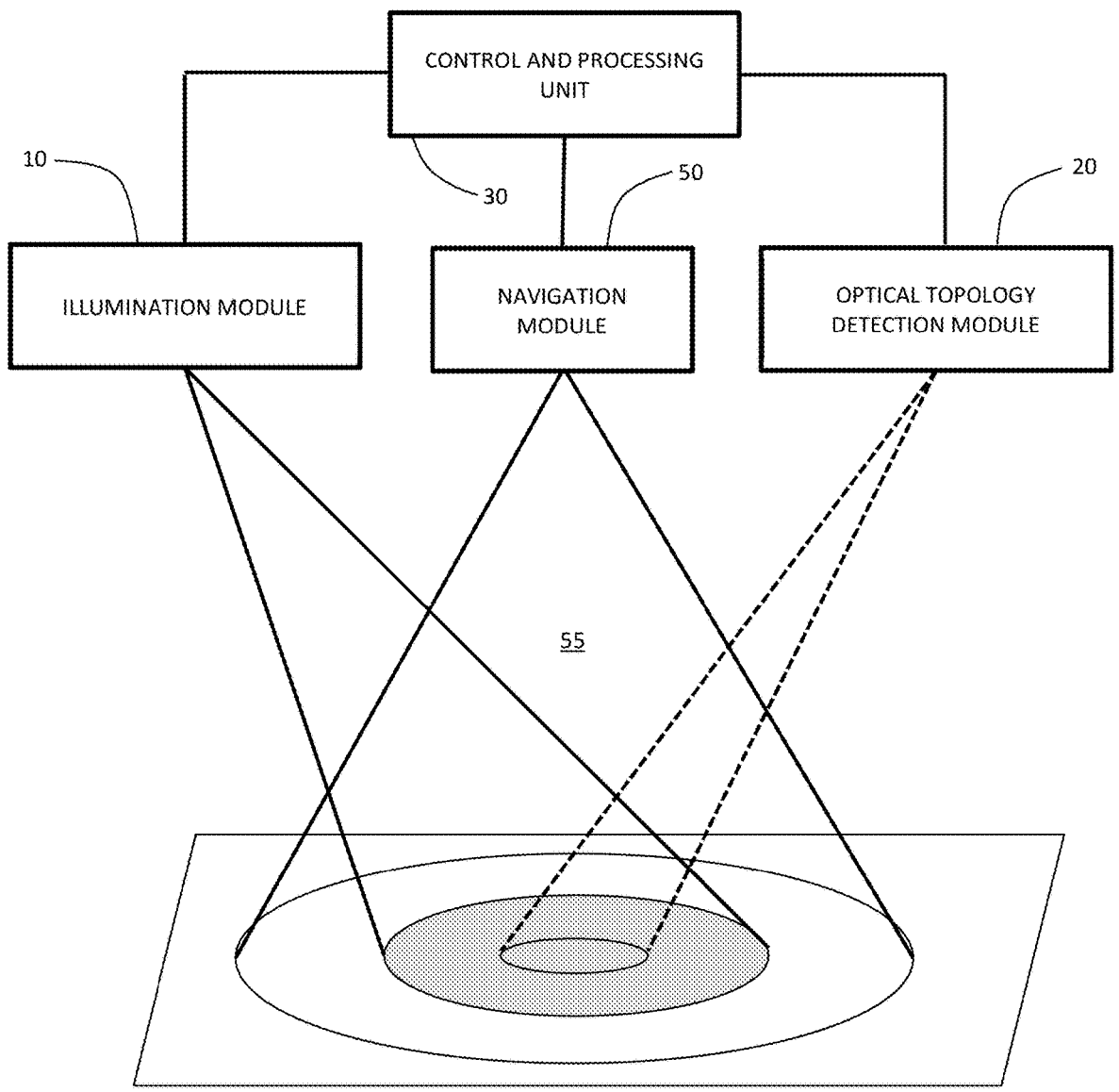
FIG. 8B is a block diagram showing another example implementation of a composite system showing shadow free illumination module, optical topology detection module and navigation module, which are controlled by a control and processing unit.

Alternatively, modules 10, 20 and 50 may be controlled by an external control and processing unit 30, for example, in the manner shown in FIG. 8B where navigation module 50 tracks objects within imaging volume 55.

Figure 9:
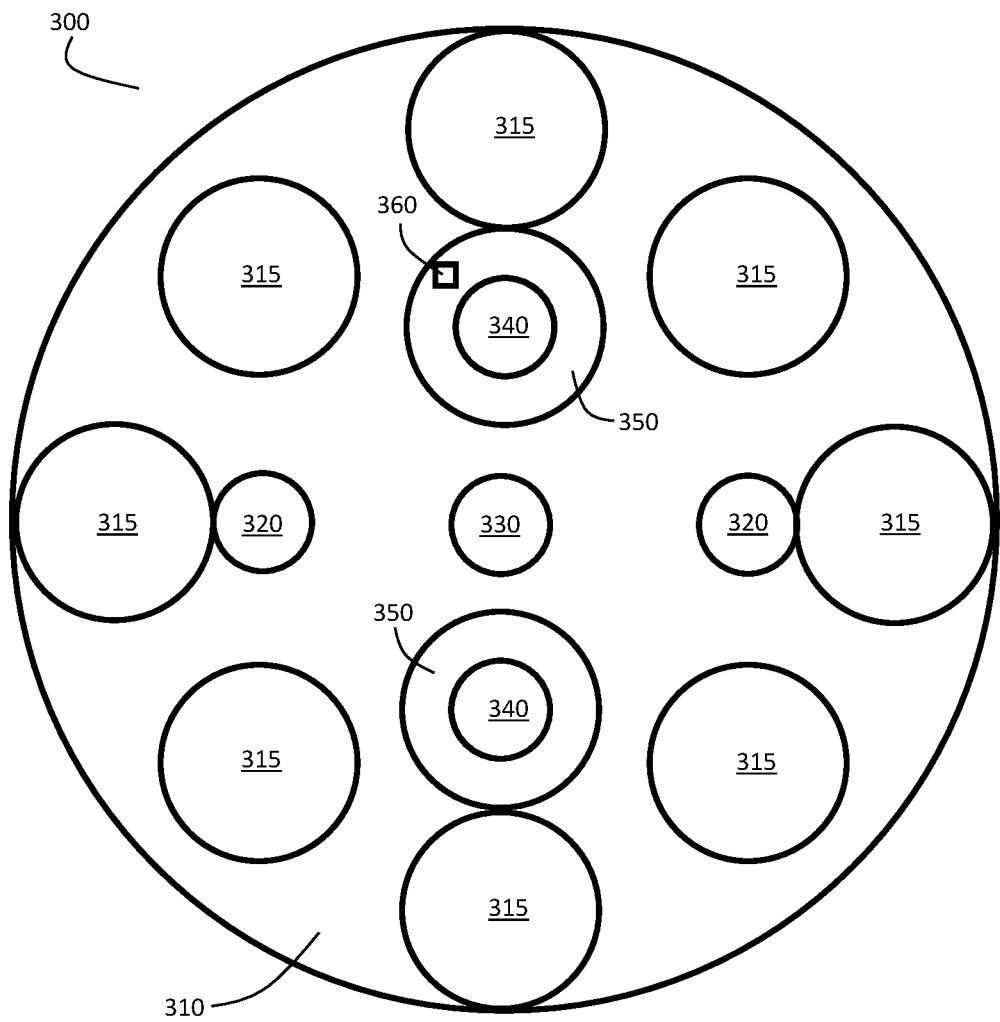
FIG. 9 is an illustration of an example composite system provided in a rigid housing (including lighting, structured light and navigation), where the view shows a plan view of the base portion of the housing.
Figure 10:
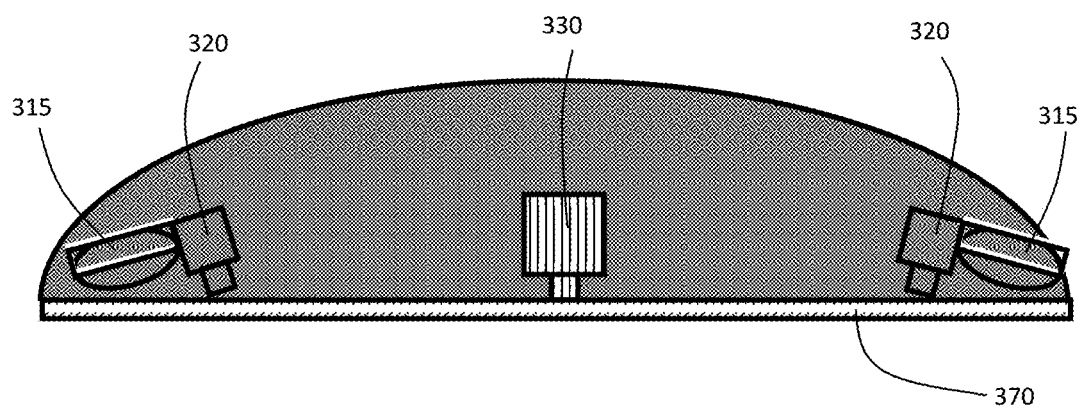
FIG. 10 is an illustration of a cross section of an example composite system (lighting, structured light and triangulation), in which the plane shown is that of the structured light cameras.
Figure 11:
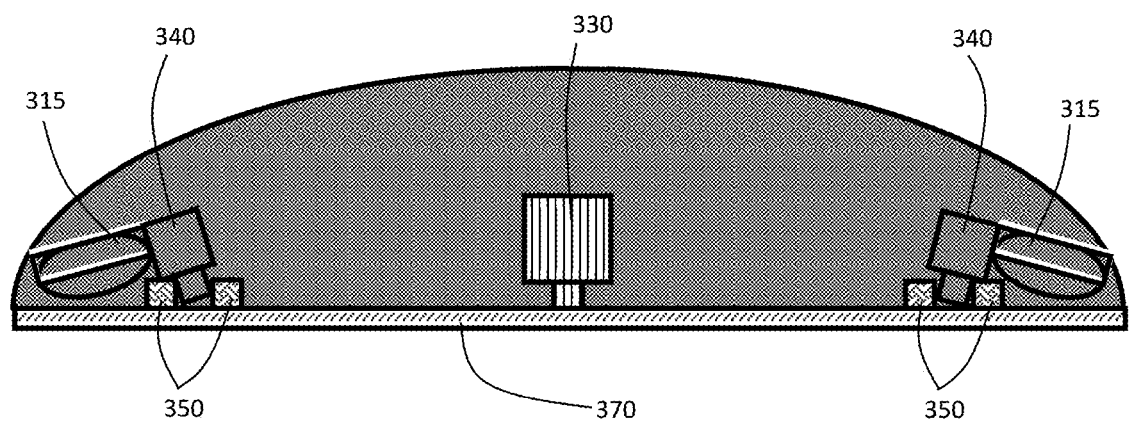
FIG. 11 is an illustration of a cross section of an example composite system (lighting, structured light and triangulation), in which the plane shown is that of the triangulation cameras.

FIGS. 9, 10 and 11 illustrate an example system implementation 300, in which each of the modules is held in a rigid housing 310. Housing 310 includes a base portion (shown in plan view in FIG. 9) configured to support components of illumination module 10 and optical topology detection module 20. In this example embodiment, the illumination module includes one or more light sources, such as LED arrays 315. Light sources 315 may be arranged symmetrically or asymmetrically about the base portion to provide substantially shadow-free illumination of the specified area. In one embodiment, one or more of the light sources 315 are arranged in a peripheral region of base portion of the housing. The power supply and modulation circuitry, which were described previously, are not shown in the Figure (these components may be either stored in the housing itself or in one or more separate modules).

As seen in FIG. 10, the base portion 370 of housing 310 may include a transparent window, to allow for illumination, projection and acquisition of images. Alternatively, apertures for each of the individual optical subcomponents can be provided in base portion 370 to allow for optical transmission.

The example implementation shown in the FIG. 10 includes a structured light system, which is includes cameras 320 and a structured light projection system 330, which consists of an optical source and a structured light projector. Cameras 320 and projection system 330 are oriented such that they are focused at the center of the shadow-free illumination field at specified distance, as shown, for example, in FIG. 9. For example, projection system may be supported near a central region of the base portion, and cameras 320 may be distributed between the central region and the peripheral region of the base portion. Cameras 320 and projection system 330 are linked to a computer, or processing system using a connection interface such as wireless, or using a physical connection such as USB, GigE, Firewire, and DVI.

Computing module 30, described above, is not shown in FIGS. 9 to 12, but it is to be understood that it may be located in close proximity to the integrated system, such as within housing 310, or further from the housing, such as in an external computing device.

Navigation module 50 may be a commercially available system such as the NDI Polaris Vicra, or a variant thereof.

In some embodiments, navigation module 50 may be recessed and/or moved off-axis relative optical topology module 20 to accommodate a housing of navigation module 50. In one example implementation, as further shown in the cross-sectional views provided in FIGS. 9 and 11, navigation module 50 may include a calibrated stereo pair of near-infrared navigation cameras 340 and near infrared LED arrays 350.

Navigation cameras 340 may be oriented such that they are able to triangulate the position of passive or active fiducial markers in a region centered on the illumination field. In one embodiment, in order to ensure that the operation of navigation module 50 does not interfere the operation of optical topology detection module 20, which may or may not be based in the IR part of the spectrum, an IR-sensitive photodiode or other suitable detector may be positioned close to the near-infrared LED array 350. For example, photodiode 360 may be employed to detect when navigation system 50 is emitting light, and to optionally provide a signal to computing module 30 for controlling and coordinating the timing of the operation of optical topology detection module 20 to avoid interference. In other embodiments, in which computing module is interfaced with each of illumination module 10, optical topology detection module 20, and navigation module 50, the direct control of each subsystem may be achieved without the need for photodiode 360.

In one embodiment, the initiation of acquisition by the optical topology detection module 20 may be controlled, by the control and processing unit based on periodic motion of the patient that is monitored.

In one example implementation, this monitored periodic motion can be used (e.g. received and processed) by the control and processing unit to trigger the optical topology detection module 20 to begin acquisition of a given structured light sequence (or subset of patterns) at a particular time point during the motion cycle (such as a breathing cycle) in order to capture topology data that is synchronized in time with the patient motion, such that acquisition of optical topology detection light is performed during a portion of a cycle of motion of the patient, while maintaining the operation of the illumination system during the cycle of motion.

In some embodiments, the acquisition of the optical topology data can be controlled based on the monitored patient motion such that optical topology data is only acquired when the speed of motion of the patient (e.g. of the relevant portion of the patient that is to be imaged) is below a pre-selected threshold. This enables the acquisition of optical topology data that is less affected by motion, with reduced or minimal artefacts.

Such an embodiment is illustrated in FIGS. 12A to 12 D and 13A to 13C. FIG. 12A shows an example measured periodic signal that is associated with the periodic motion of the patient. This signal may be employed to trigger the acquisition of optical topology data. For example, FIG. 12B shows a trigger signal 382 that is generated (e.g. by the control and processing unit) from the periodic signal shown in FIG. 12A. The trigger signal may be employed to trigger the acquisition of a sequence of structured light (optical topology) patterns.

In one example implementation, a sequence of structured light patterns may be obtained at a pre-selected delay relative to the trigger signal, such that the acquisition occurs when the motion of the patient at a point during the motion cycle when the motion is slow and unlikely to produce artefacts. Such an example implementation is shown in FIG. 12C where the structured light sequence is acquired when the motion is near a minimum. It is noted that during time duration 382, both optical topology acquisition and illumination are performed at high frequency (as shown in FIGS. 6A to 6D), while during the rest of each cycle, illumination is provided at high frequency in the absence of optical topology acquisition.

In another example implementation, the sequence of structured light patterns may be initiated at a point in time after the trigger signal when the speed of motion is below a pre-selected criterion. For example, the time durations 382 shown in FIG. 12C may be selected based on the speed being below a pre-selected threshold. FIG. 12B shows the derivative 383 of the monitored signal, which is proportional to the speed of motion of the patient. An example speed threshold is shown at 384, and acquisition of optical topology (FIG. 12C) may be initiated when the speed of motion falls below this threshold value after the trigger signal is received, corresponding to the regions shown in the acquisition regions (grey areas) 386.

Another example implementation is depicted in FIGS. 13A to 13C in which, the position value of the periodic signal 380 (associated with the patient position) is employed to break up/continue acquisition of structured light patterns. Referring now to FIG. 13A, a detailed view of one cycle of the position signal 380 is shown, along with a position threshold 391 and acquisition region 392.

FIG. 13B shows the associated time dependence of the acquisition of the optical topology data. Optical topology data is acquired when the position of the patient (e.g. as determined based on the signal 380) falls within a pre-selected position range, such as between a minimum value and threshold 391 For example, as shown in FIG. 13B, optical topology data is only obtained for when the patient position is at near the minimum position, where the motion of the patient is slow. Optical topology data is not acquired when the position of the patient is outside of the pre-selected position range, corresponding to region 394, where the missing optical topology acquisition events are shown in dotted lines.

In the example embodiment shown in FIG. 13B, the topology patterns making up a full sequence are grouped into six groups of patterns, identified in the figure as S1-S6. The projection, and detection, of groups of topology patterns is halted, and delayed, when the signal 380 lies outside of the pre-selected position. The projection, and detection, of groups of topology patterns resumes once signal 380 falls within the pre-selected region. This can be seen for example, as the group of patterns S4 precedes region 394, which resumes with the group of patterns S5 after region 394. As shown in FIG. 13C, the illumination continues during time durations 392 and 394, such that the operator does not perceive a noticeable change in illumination.

It is noted that if the time duration available for topology acquisition within a given motion cycle is only a fraction of the time needed to acquire a full set of patterns, then two or more motion cycles may be employed to acquire the full set of patterns.

In one example implementation, optical topology data may be captured by utilizing the tracking of the periodic motion of the patient to trigger the initiation of the acquisition of an optical topology sequence one or more points in time during each cycle of periodic motion of the patient—in other words, the sequence may be obtained at one or more phases during each cycle of the periodic motion of the patient. The resulting topology data, obtained over multiple cycles of periodic motion of the patient, can then be used to display, and/or retrospectively reconstruct, the time evolution of the optical topology information at any of the one or more phases.

In other embodiments, the motion of the patient may be monitored, as described above, in order to detect the occurrence of sudden motions using the navigation/tracking system. Such sudden motions may result in the corruption of optical topology data by motion artefacts. In response to the detection of such a sudden motion, the controller may perform one or more actions, such as, but not limited to, notifying the user or operator (for example, of the need for re-acquisition), and/or automatically controlling the system to perform re-acquisition.

In one example implementation, a sudden motion may be detected by calculating the speed or velocity of the patient motion (as shown above). For example, if the speed during acquisition exceeds a pre-selected threshold, then the controller may perform one or more actions. The threshold may be user defined or based on the intrinsic parameters of the imaging system. For example, if the optical topology system has an isotropic resolution of 300 um and that the time needed for acquisition was 100 ms, then it would be preferable if all patterns were acquired during a time duration when the motion is less than 300 um in 100 ms, or had a speed of less than 3 mm/s.

In one embodiment, the motion of the patient may be monitored, for example, based on input or feedback provided by the navigation module 50. For example, one or more fiducial markers (such as markers associated with a stereotactic/reference frame) that are attached or otherwise secured to the patient at or near a site of interest (e.g. fixed relative a relevant portion of the patient's body) may be tracked by the navigation module 50, such that periodic motion of the patient (e.g. due to breathing or heartbeat) can be monitored.

Other methods for strategically triggering the acquisition of the optical topology system could include directly receiving periodic signals from ECG system or ventilation unit.

Alternatively, the optical topology detection system itself could be used to track the periodic motion with sufficient temporal resolution. For example, a shorter set of structured light patterns than the full set employed for surface reconstruction (e.g. the first 6 patterns of a gray code sequence, de brujin sequence etc.) could be used to generate a sparse set of points in a relatively shorter period of time (for example, <60 ms). This sparse set could be used to continuously track the bulk motion of the tissue and to trigger when a high density topology is to be acquired.

In a further embodiment, the position of the one or more fiducial markers can be monitored in order to determine whether the site or region of interest to be imaged by optical topology, (which may be assumed to be close to the location of the reference frame) is within or near the optimal imaging volume associated with the optical topology detection system. For example, if the site or region of interest is not within or near the imaging volume, then the acquisition by the optical topology system can be disabled, and the user may be notified that the system needs to be repositioned. Alternatively, the optical topology detection system may be automatically repositioned based on feedback from the navigation system.

FIGS. 14A to C show system 400, which is a variation of system 300 shown in FIGS. 9 to 11. System 400 includes one or more additional cameras 440 for navigation (e.g. tool tracking) and one or more structured light imaging cameras 420 to increase the robustness of the system to line of sight obstructions. The figure shows an example implementation with two additional cameras of each type, but it will be understood that in general, one or more additional cameras of each type may be provided. In one embodiment, both navigation and structured light imaging can be performed with any pair of suitable cameras and datasets merged for better coverage of the surgical field. Additionally, NIR illumination for tool tracking and shadow free illumination modules have been merged into composite lightning panels 415/450. For example, these light panels may contain a mixture of NIR and visible wavelength LED's mounted onto a PCB substrate but may be driven by separate LED drivers. Approximate field of views for each of the modules is also shown for a typical surgical light working distance of approximately 100 cm. It will be understood that FIGS. 14A to 14C provide an example implementation of such an embodiment, and that other configurations with other numbers of components and/or positioning of components may be employed in various alternative implementations.

Figure 15A:
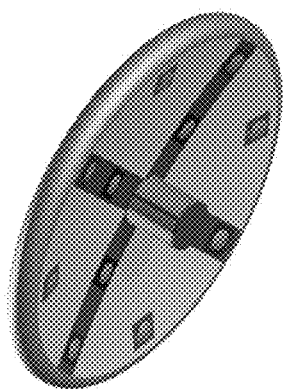
FIG. 15A and FIG. 15B shows example embodiment multiple optical topology projectors are utilized to further increase robustness to line of sight obstructions.
Figure 15B:
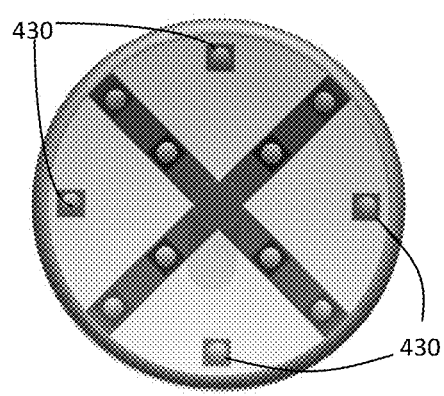

FIGS. 15A and 15B show another example embodiment where multiple optical topology projectors 430 may be utilized in order to further decrease the effects of line of sight obstruction. The multiple projectors may operate on different spectral bands and/or timing schemes to avoid cross talk during acquisition in overlapping field of views. In some embodiments, one or more projectors may be moved to enable optical topological detection from different views. The mechanism of movement may be manual or motorized. Alternatively, the projector beam path may be optically steered (manually, or automated).

Reconstructions from different projector views can be combined using stereo camera calibration data in the case of stereo camera acquisition, for example, as described in Scharstein D., Szeliski R "High-Accuracy Stereo Depth Maps Using Structured Light" IEEE Computer Society Conference, Computer Vision and Pattern Recognition, 1-195, 2003. Briefly, the method involves the following steps: 1) acquire images from calibrated stereo camera pair at each projector location, 2) rectify image pairs for each projector location, 3) decode phase and/or gray code images etc. at each projector location, 4) calculate disparity maps for each projector location, 5) project disparity maps into real space using perspective transform for each projector location to generate point clouds, 6) merge point clouds from all projector locations. This can be accomplished as all point clouds share a common origin and orientation such as one of the cameras in the calibrated stereo pair. In the case of single camera acquisitions the projector location, relative to the camera, must be tracked or known a priori to merge the reconstructions.

It is important to note that when the structured light is accomplished in the visible spectrum and there is no spectral overlap between the navigation and optical topology detection module spectral bands, synchronization is not necessarily required, as these two systems can operate independently without producing spectral cross-talk. However, when spectral bands of the structured light and navigation system overlap, such as the case where they both employ near-IR spectral bands, synchronization between the optical topology module 20 and navigation module 50 is beneficial to reduce cross-talk between modules.

Such an embodiment is illustrated in FIG. 16, where the navigation module on-time 230 is positioned in the timing diagram such that this falls within the period of the primary lighting on time (LED) 225. Therefore, synchronization will occur in a serial fashion such that the projector illumination 215 occurs at a different time point than the navigation module on time 230, where their respective near-IR spectral bands do not temporally overlap to stop the possibility of spectral cross-talk.

FIGS. 17A to 17F show an additional embodiment of a timing diagram when an embedded photodiode (see photodiode 360 in FIG. 9) controls the triggering of the optical topology module 20 and navigation module 50, which both operate in the NIR spectral regime. According to the present embodiment, these modules operate at different times to reduce potential cross-talk between the spectrally similar near-IR signals. As in the previous embodiment, the projection system can be triggered using the master clock, which subsequently projects the pattern and sends a trigger to turn off the primary lighting on time (LED) 220 and begin the camera exposure 225. When a structured light acquisition is requested the system waits for the falling edge of the photodiode response 235 before the master clock 210 begins outputting the main synchronization signal. Ideally, all of the patterns produced during the projector on-time 215 are projected between two adjacent navigation system exposures, which are typically very short (~1 ms) leaving a large amount of dead time between exposures (~50 ms).

However, in the case when a large amount of patterns are required and exceed the overall time between the navigation module on time 230, the patterns can be broken up into packets of patterns to be displayed over multiple adjacent navigation exposures (perhaps due to limitations in projection and camera speeds). Therefore, in such an embodiment, the sequence is broken into smaller packets of patterns, which can temporally fit between navigation system exposures.

For example, referring again to FIGS. 17A to 17F if the period of the navigation module on-time 230 (i.e. the time duration between successive activations of the navigation module, not the on-time duration of a given activation of the navigation module) is ~33 ms, and 24 images are to be projected at a frame rate of 100 Hz, the overall required time for the projection of 24 images would be ~240 ms, which is longer than the navigation module on time 230 and would cause problems with overall system trigger. Therefore, with the addition of a hardware or software delay 205, the system may be configured to split the 24 images into 8 packets of 3 images, where the 24 images would be displayed over 8 complete periods of the navigation module on time 230 such that near-IR cross talk does not occur. Alternatively, a triggerable shutter could also be used to block the navigation module so that near-IR cross talk does not occur. It is to be understood that the preceding example is but one specific implementation of a method in which multiple structured light images (and illumination exposures) are interleaved between navigation exposures, and it is to be understood that there may be a wide range of different implementations of this embodiment.

Figure 18:
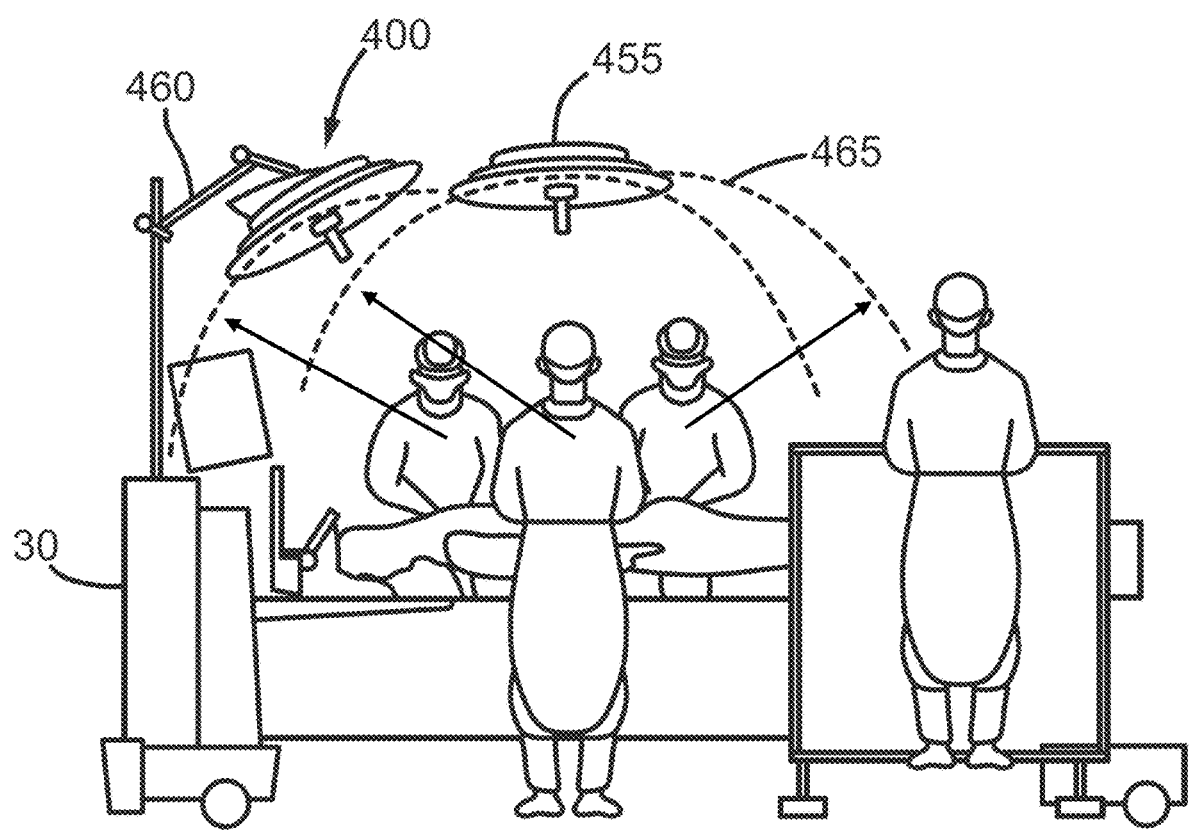
FIG. 18 is an illustration showing a schematic of an example integrated illumination and optical topology system employed in an operating room environment.

FIG. 18 is a schematic of the example integrated illumination and optical topology system represented at 400. This system could be mounted via an articulating arm 460, which could be physically attached to a cart as shown. Control and processing unit 30 could be housed, for example, within this cart, or alternatively, for example, in the case where the integrated illumination and optical topology system 400 is mounted on a wall or hung from the ceiling on a similar articulating arm 460, control and processing unit 30 could be located within or outside of the surgical theatre.

A suitable working distance and location of the field of view can be determined and/or maintained by the combination of surgeon(s) observing optically emitted calibration patterns from the system 400. For example, the surgeon could identify the center and working distance of system 400 through direct visual inspection of a pattern with sharp edges (e.g. checkerboard, crosshair, etc.), which may be projected in a particular color/wavelength. In this example, the calibration pattern is projected without any of the aforementioned modulation schemes so that it is clearly visible to the surgeon. The illumination light source may also be turned off during this process in order to make the calibration pattern more clearly visible.

For example, in one implementation, the projection of a calibration pattern could be initiated when the operator or surgeon actuates a mechanical switch or sensor (e.g. the operator grips a handle or depresses a foot pedal). After the operator or surgeon stops actuating the switch or sensor, the system reverts to an "invisible mode" where structured light patterns are hidden according to the embodiments described above. In an alternative embodiment, a pattern for positioning may be projected such that it is invisible to the operator or surgeon (according to the methods described herein) but, where the pattern may be indirectly visualized on a display using the output from the synchronized cameras.

Alternatively, the surgeon may directly visualize the cameras' output image/video feeds through the system's computer monitor to ensure that the images/videos acquired by the cameras are in focus. Generally, if all components of the system are properly positioned and calibrated, the images/videos from the cameras of the patient's anatomy, as well as any projected patterns made visible to the surgeon as described above, should be in focus. These procedures ensure that the system is at a suitable working distance from the target before acquiring structured light data. In an alternative embodiment, two or more visible lasers can be attached to system 400 and aimed towards the surgical field so that the lasers intersect at the center of the suitable working volume. This helps the surgeons with orienting system 400 during surgery by aligning the two laser dots until they overlap on surfaces of regions of interest in the surgical field.

Additional surgical lights 455 could be synchronized via triggering schemes as seen in FIGS. 8, 16, and 17 such that the ambient light in surgical theatre can be controlled. These additional lights could be in the form of, but not limited to, overhead surgical lights, ceiling mounted lights, wall lights, and headlamps.

The dashed arrows 465 on FIG. 18 represent the range of motion of the illumination modules and approximately 100 cm distance from the illumination and optical topology system from the patient. The solid arrows indicate which surgeons would be in the optimal position to move the optical topology detection system 400 and surgical lights 455 to specified locations, via an articulating arm 460. These potential positions lie within the semi-hemisphere represented by positioning arcs 465.

In another embodiment, the system could detect the ambient light characteristics (for example intensity, modulation frequency and spectrum) within the optical topology detection field 85 in order to adjust the illumination and modulation parameters of the optical topology detection module 20 to improve optical topology imaging. Accordingly, in one embodiment, the detected level of ambient light may be provided as a feedback parameter to the control and processing unit, in order to actively control the intensity and/or duration of the illumination exposures, such as to achieve a pre-determined intensity and/or time duration ratio of the illumination light to the light from the optical detection system, or to ensure that the signal to noise ratio of detected light exceeds a given value.

For example, in one implementation, the illumination and modulation parameters may be adjusted to achieve a pre-determined intensity and/or time duration ratio of the illumination light and the light from the optical detection system and the ambient lighting level. The system may display a warning (for example through user interface 32) to the operator to adjust the ambient lighting conditions when the measured ambient light levels are beyond a specified value, or outside of a pre-determined range. These ambient light characteristics could be detected via optical topology cameras 26 or another photoactive device such as a photo-detector or spectrometer.

In some embodiments, in which the synchronization of the illumination module and the topology detection module is performed in an open loop fashion via timing alone, a small time delay may be added after turning off the illumination light prior to activating the optical topology detection module, if there is a possibility of time-dependent decay of the illumination intensity after the illumination light source is turned off (e.g. due to luminescence).

Figure 19:
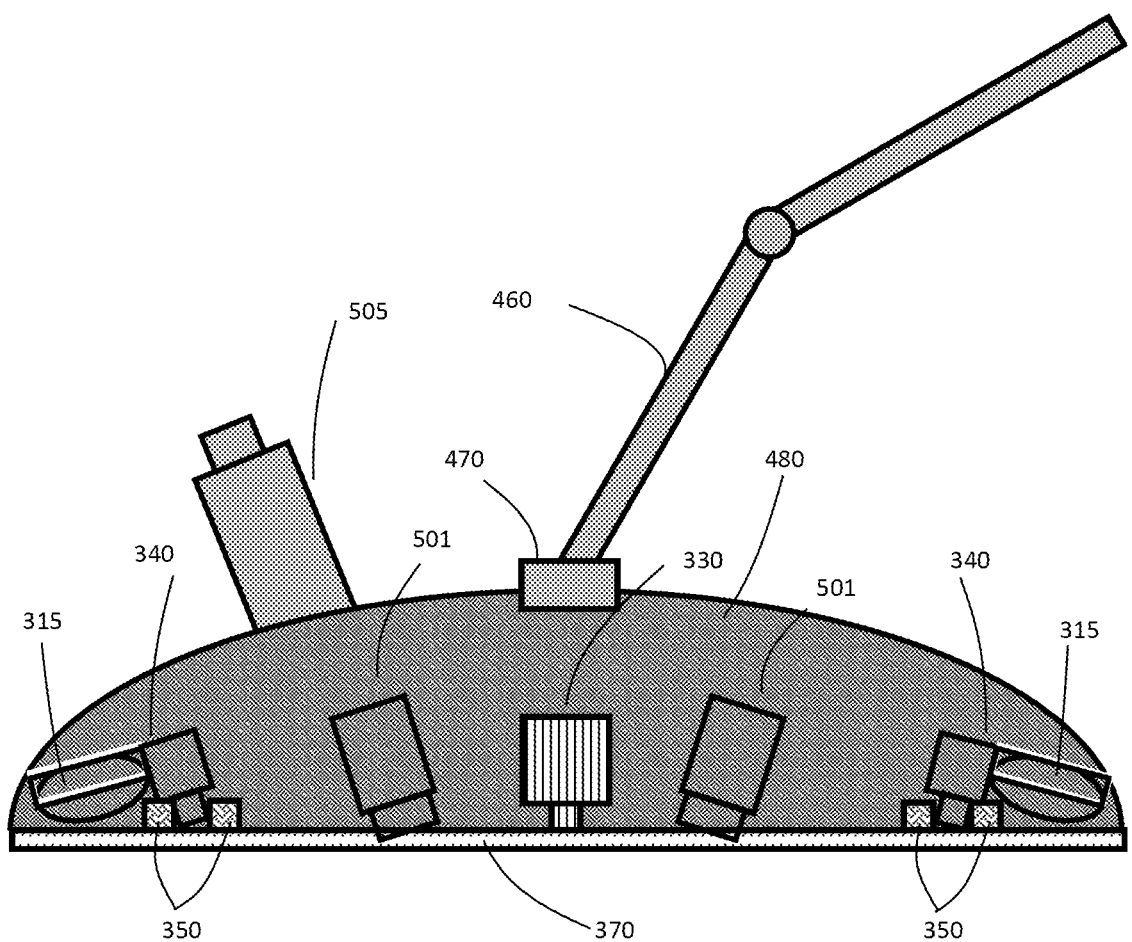
FIG. 19 is a schematic of an example integrated illumination and optical topology system integrated into a surgical microscope.

In another embodiment, the system can be adapted to act as a surgical microscope. FIG. 19 is an example schematic of such as a system. Articulating arm 460 is attached to system enclosure 480 via an attachment mechanism that may include a pivot joint such as a ball joint or universal joint, which may be locked in position. This allows the system to be positioned on top of a region of interest. Two additional cameras 501, which may be of higher resolution than the navigation cameras 340, are used to provide a binocular, high resolution view of the surgical field. Typical magnifications for cameras 501 are 1× to 5×.

Figure 20:
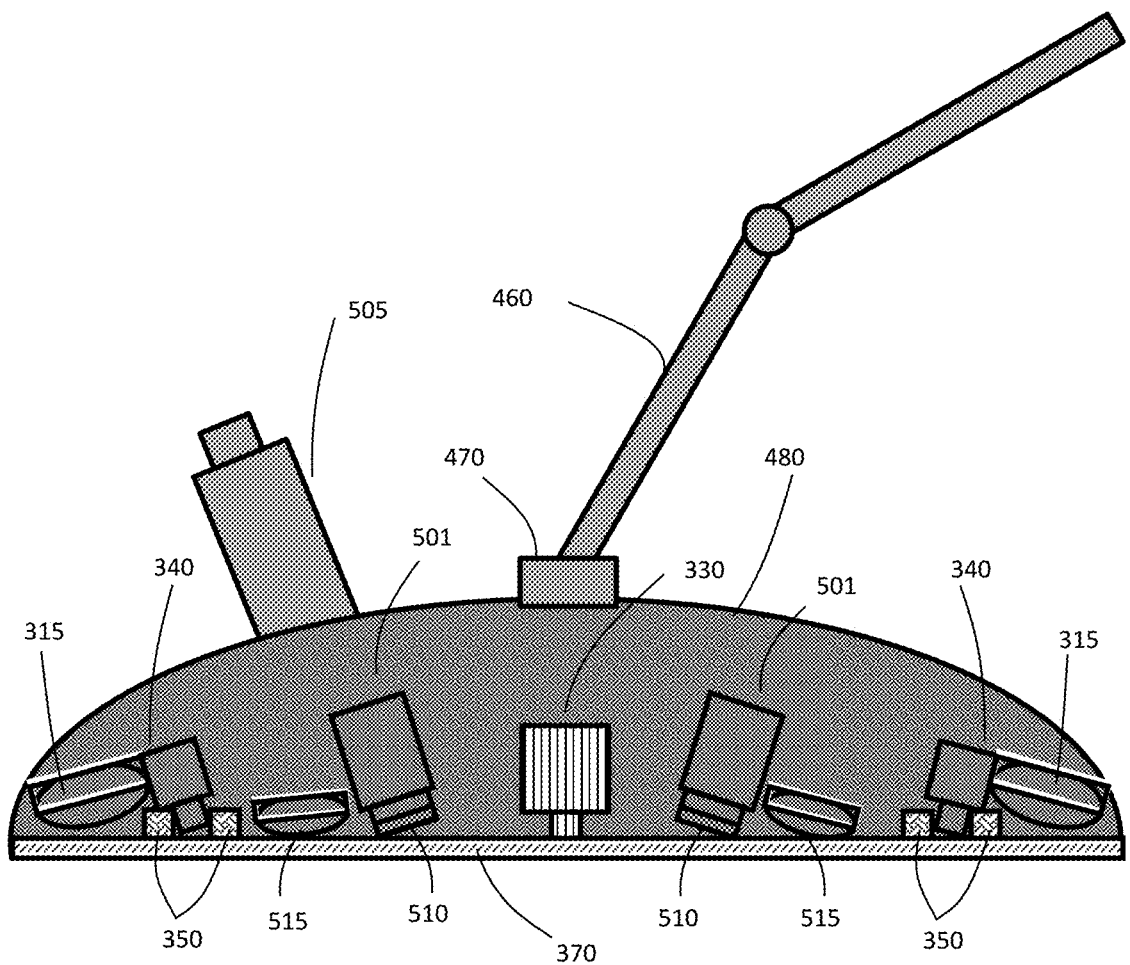
FIG. 20 is a schematic of an example integrated illumination and optical topology system integrated into a surgical microscope for fluorescence imaging.

In another example embodiment, the surgical microscope may be adapted for fluorescence imaging. FIG. 20 shows an example schematic of such system. Optical filters 510 are added to cameras 501. Additional light sources 515, which act as the excitation light, are also added to the system. A non-limiting example is the fluorescence imaging of fluorescein isothiocyanate. In this example, the light sources 515 would be centered at ~490 nm, and the filters centered at ~510 nm. The light source may for example, be blue LEDs. The filters for example, may be bandpass filters. The light sources may be turned on in an on-demand fashion. Alternatively, the light sources may be modulated by the modulation scheme described in this patent, for example, perform structured light acquisition and fluorescence imaging in an interleaved fashion.

A live stream of the video cameras 501 may be displayed by various means. One example is a head mounted display. Another example is an eye piece 505 with two view ports, one for each eye, similar to standard surgical microscopes. A third example is a 3D monitor. The eye piece 505 may be attached directly on top of enclosure 480. In this case, the surgeon can operate with their hands between the enclosure 480 and the region being operated on, while looking down into the eyepiece.

This integrated system allows surface topology imaging, tool tracking, and illumination to be performed simultaneously. Navigation information, such as surgical tool location relative to preoperative images, obtained using the methods described in this invention, may be overlaid on top of the video stream from cameras 501. Visualization of tool tracking information can take the form of a semi-transparent visual layer that is overlaid on top of the live stream from the video cameras. Alternatively, a smaller window can be present, for example, in the lower right corner of the video stream, that completely blocks the video stream in that portion of the visualization. This smaller window would show navigation information such as where a tool is relative to a set of preoperative images. The size and position of this navigation window can vary depending on surgeon preference.

The systems and methods described above may be employed for a wide range of medical imaging applications. Additional medical applications of the system and methods described herein include colonoscopy, endoscopy and bronchoscopy procedures. For example, structured light imaging systems can be integrated into tools such as endoscopes, bronchoscopes and exoscopes to provide comprehensive visualization of the topology of luminal surfaces without disruption to the operator's visual field. Additionally, the modulation schemes described herein can also be combined with fluorescence based imaging for added functional contrast.

The embodiments described here can also be employed in other non-medical applications, in which surface topology acquisition is required in an illuminated environment. For example, digitization of actors' physical features in 3D for video games or other forms of media can make use of structured light imaging in real time. The system and methods described can be used to prevent the visual disturbance to the actors caused by the projected light. It may also be possible to make use of these embodiments in other 3D surface acquisition of the whole or parts of the human body, for example, in biometric or security applications to minimize the discomfort of the subjects being inspected.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. An integrated surgical system for optical topology detection, illumination, and tracking, comprising:
   a surgical illumination system comprising one or more illumination light sources for illuminating a region of interest with illumination light;
   an optical topology detection system comprising a structured light projection device for projecting optical topology detection light comprising structured light patterns onto the region of interest and one or more optical topology detection cameras for imaging optical topology detection light scattered or reflected from the region of interest;
   an optical tracking system comprising a plurality of tracking cameras for detecting tracking light associated with one or more fiducial markers;
   wherein at least a portion of the spectral content of the illumination light from said surgical illumination system is within an optical detection bandwidth of said optical topology detection system;
   wherein at least a portion of the spectral content of the tracking light detected by said optical tracking system is within the optical detection bandwidth of said optical topology detection system; and
   one or more processors configured to:
      provide one or more control signals for repeatedly triggering interleaved operation of said optical topology detection system with said surgical illumination system; and
      synchronize the operation of said optical topology detection system, said surgical illumination system and said optical tracking system, according to the one or more control signals, such that said optical topology detection system detects optical topology detection light in the absence of the illumination light and tracking light.

2. The integrated system according to claim 1 wherein said one or more processors are configured to control the operation of said optical tracking system.

3. The integrated system according to claim 2 wherein said one or more processors are configured to synchronously control the operation of said surgical illumination system and said optical tracking system.

4. The integrated system according to claim 3 wherein said one or more processors are configured to control said surgical illumination system such that said surgical illumination system is intermittently activated during a series of illumination time intervals, and to control said optical tracking system such that said optical tracking system is activated during a portion of each illumination time interval.

5. The integrated system according to claim 1 wherein said optical tracking system comprises one or more tracking light sources, and wherein said integrated surgical system further comprises:
a photodetector configured to detect the emission of tracking light from said one or more tracking light sources;
wherein said one or more processors are configured to control the operation of said optical topology detection system and said surgical illumination system such that said optical topology detection system detects optical topology detection light when said photodetector detects the absence of tracking light.

6. The integrated system according to claim 5 wherein said one or more processors are configured to control the operation of said optical topology detection system such that said optical topology detection system is activated to detect optical topology detection light after a prescribed time delay following detection of the absence of tracking light by said photodetector.

7. The integrated system according to claim 1 wherein said one or more processors are configured such that said surgical illumination system and said optical topology detection system are intermittently activated two or more times between successive activations of said optical tracking system.

8. The integrated system according to claim 1 wherein said structured light projection device is configured to project an ordered series of patterns for topology detection, and wherein two or more patterns are projected during the time between successive activations of said optical tracking system.

9. The integrated system according to claim 1 wherein said structured light projection device is configured to project an ordered series of patterns for topology detection, and wherein all of the patterns are projected during the time between successive activations of said optical tracking system.

10. The integrated system according to claim 1 wherein said structured light projection device is configured to project an ordered series of patterns for topology detection, and wherein one pattern is projected during the time between at least one pair of successive illumination cycles.

11. The integrated system according to claim 1 wherein said structured light projection device is configured to project an ordered series of patterns for topology detection, and wherein two or more patterns are projected during the time between at least one pair of successive illumination cycles.

12. The integrated system according to claim 1 wherein said structured light projection device is configured to project an ordered series of patterns for topology detection, and wherein all of the patterns are projected during the time between at least one pair of successive illumination cycles.

13. The integrated system according to claim 1 wherein said one or more processors are configured to control said surgical illumination system and said optical topology detection system such that the illumination light and the optical topology detection light are interleaved at a sufficiently high frequency that the illumination light is perceived as being continuous in time by an observer.

14. The integrated system according to claim 13 wherein the duration of the optical topology detection light is controlled relative to the duration of the illumination light in order to reduce visual disruptions perceived by the observer.

15. The integrated system according to claim 13 wherein the sequence of light patterns is selected to reduce visual disruptions perceived by the observer.

16. The integrated system according to claim 15 wherein the intensity of projected light patterns is controlled relative to the intensity of the illumination light in order to reduce visual disruptions perceived by the observer.

17. The integrated system according to claim 1 wherein said plurality of tracking cameras are oriented such that they are centered on an illumination field of said illumination light sources.

18. The integrated system according to claim 1 wherein said optical tracking system is rigidly mounted to said optical topology detection system such that a tracking volume associated with said optical tracking system is fixed relative to an optical topology detection field of said optical topology detection system.

19. The integrated system according to claim 18 wherein said optical topology detection system and said optical tracking system are supported by a rigid housing.

20. The integrated system according to claim 19 wherein said rigid housing is further adapted to rigidly support said surgical illumination system.

21. The integrated system according to claim 20 wherein said illumination light sources are a plurality of illumination light sources, and wherein said optical tracking system comprises a plurality of tracking light sources, and wherein said plurality of illumination light sources and said plurality of tracking light sources are spatially arranged as a plurality of composite lighting panels.

22. The integrated system according to claim 19 wherein said rigid housing is supported on an articulating arm for varying a position and/or angle of said rigid housing.

23. The integrated system according to claim 19 wherein said optical tracking system comprises a tracking system housing that is rigidly supported by said rigid housing, and wherein said optical tracking system is recessed or off-axis relative to said optical topology detection system to accommodate said tracking system housing.

* * * * *